US009234855B2

(12) United States Patent
Watanabe

(10) Patent No.: US 9,234,855 B2
(45) Date of Patent: Jan. 12, 2016

(54) APPARATUS, X-RAY IRRADIATION METHOD, AND STRUCTURE MANUFACTURING METHOD

(71) Applicant: Takashi Watanabe, Tokyo (JP)

(72) Inventor: Takashi Watanabe, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 407 days.

(21) Appl. No.: 13/644,384

(22) Filed: Oct. 4, 2012

(65) Prior Publication Data

US 2013/0083896 A1    Apr. 4, 2013

Related U.S. Application Data

(60) Provisional application No. 61/548,449, filed on Oct. 18, 2011.

(30) Foreign Application Priority Data

Oct. 4, 2011    (JP) .................. 2011-220258

(51) Int. Cl.
*H01J 35/10* (2006.01)
*G01N 23/04* (2006.01)
*H05G 1/02* (2006.01)
*H01J 35/14* (2006.01)

(52) U.S. Cl.
CPC ............... *G01N 23/04* (2013.01); *H05G 1/025* (2013.01); *H01J 35/14* (2013.01); *H01J 2235/1204* (2013.01); *H01J 2235/1216* (2013.01); *H01J 2235/1262* (2013.01)

(58) Field of Classification Search
CPC ............. G01N 23/04; H01J 2235/1204; H01J 2235/1216; H01J 2235/1262; H01J 35/14; H05G 1/025

USPC .......................................................... 378/199
See application file for complete search history.

(56) References Cited

U.S. PATENT DOCUMENTS

| 5,594,768 | A | 1/1997 | Fujii et al. | |
| 6,377,659 | B1 * | 4/2002 | Snyder et al. | 378/142 |
| 6,400,799 | B1 * | 6/2002 | Andrews | 378/141 |
| 6,836,535 | B2 * | 12/2004 | Toth et al. | 378/159 |
| 6,993,117 | B2 | 1/2006 | Toth et al. | |
| 7,186,021 | B1 | 3/2007 | Breham et al. | |

(Continued)

FOREIGN PATENT DOCUMENTS

| JP | 62-232547 | 10/1987 |
| JP | H04-038453 Y2 | 7/1989 |

(Continued)

OTHER PUBLICATIONS

International Search Report issued in application PCT/JP2012/075615, Oct. 30, 2012, 5 pages.

(Continued)

*Primary Examiner* — Michael Maskell
(74) *Attorney, Agent, or Firm* — Finnegan, Henderson, Farabow, Garrett & Dunner, LLP

(57) ABSTRACT

There is provided an apparatus configured to irradiate an object with an X-ray and detect a transmission X-ray transmitted through the object, including: a chamber member defining a first space; and a first supply port arranged in the first space to supply a temperature-controlled gas to a part of an X-ray source configured to irradiate the object with the X-ray.

30 Claims, 20 Drawing Sheets

(56) References Cited

U.S. PATENT DOCUMENTS

| | | | |
|---|---|---|---|
| 7,311,439 | B2 | 12/2007 | Müller |
| 2002/0146092 | A1* | 10/2002 | Richardson et al. .......... 378/130 |
| 2002/0154728 | A1 | 10/2002 | Morita et al. |
| 2003/0198319 | A1 | 10/2003 | Toth et al. |
| 2003/0199757 | A1* | 10/2003 | Toth et al. .................... 600/425 |
| 2004/0202287 | A1 | 10/2004 | Muller |
| 2005/0100128 | A1 | 5/2005 | Hilderscheid |
| 2009/0268869 | A1 | 10/2009 | Hadland |
| 2010/0033694 | A1* | 2/2010 | Kamiya et al. ................. 355/30 |
| 2010/0111259 | A1* | 5/2010 | Van Der Ende .............. 378/142 |
| 2010/0220908 | A1 | 9/2010 | Khare et al. |
| 2012/0155606 | A1 | 6/2012 | Simon |

FOREIGN PATENT DOCUMENTS

| | | | | |
|---|---|---|---|---|
| JP | H02-260354 | | 10/1990 | |
| JP | 04-038453 | | 7/1992 | |
| JP | H04-38453 | | 9/1992 | |
| JP | H04-038453 | Y2 | 9/1992 | |
| JP | 05-056958 | | 3/1993 | |
| JP | 07-306165 | | 11/1995 | |
| JP | 07306165 | A * | 11/1995 | ............. G01N 23/04 |
| JP | 10-254062 | | 9/1998 | |
| JP | 2003-173752 | | 6/2003 | |
| JP | 2003-339691 | | 12/2003 | |
| JP | 2006-073881 | | 3/2006 | |
| JP | 2007-109506 | | 4/2007 | |
| JP | 2010-185859 | | 8/2010 | |
| JP | 2010185859 | A * | 8/2010 | |
| JP | 2010-212072 | | 9/2010 | |
| WO | WO 2006-025320 | | 3/2006 | |
| WO | WO 2010-124868 | | 11/2010 | |

OTHER PUBLICATIONS

PCT Written Opinion issued in application PCT/JP2012/075615, Oct. 30, 2012, 14 pages.

Japanese Patent Office, International Search Report and Written Opinion for PCT International Application PCT/JP2012/075615, mailed Oct. 30, 2012, 14 pages.

JPO Notification of Reasons for Refusal, Patent Appl. No. 2013-537527, mailed Mar. 31, 2015.

Japanese Patent Office; Office Action in Patent Application No. 2013-537527, mailed Dec. 24, 2014, six pages.

European Search Report for Application No. 12837797.5; dated Mar. 25, 2015.

JPO Notification of Reasons for Refusal, Patent Appl. No. 2013-537527, dated May 26, 2015.

Notification of Reasons for Rejection issued by the Japanese Patent Office in corresponding Japanese Application No. 2013-537257, mailed Aug. 5, 2015 (3 pages).

Notification of Reasons for Rejection issued by the Japanese Patent Office in corresponding Japanese Application No. 2013-537527, mailed Aug. 5, 2015 (3 pages).

* cited by examiner

Fig. 10
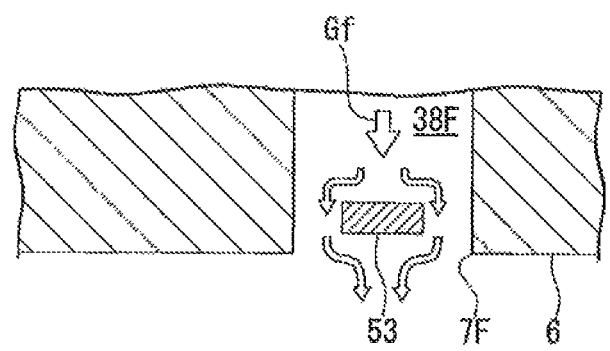
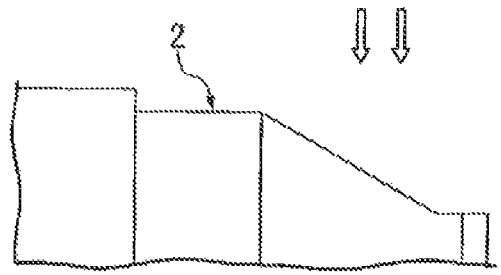
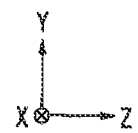

Fig. 11
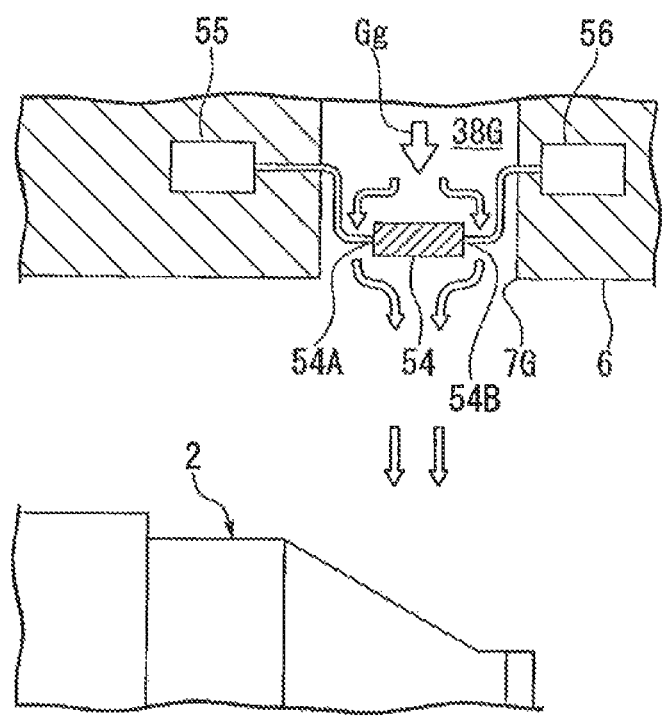
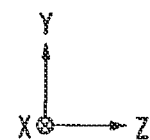

Fig. 13
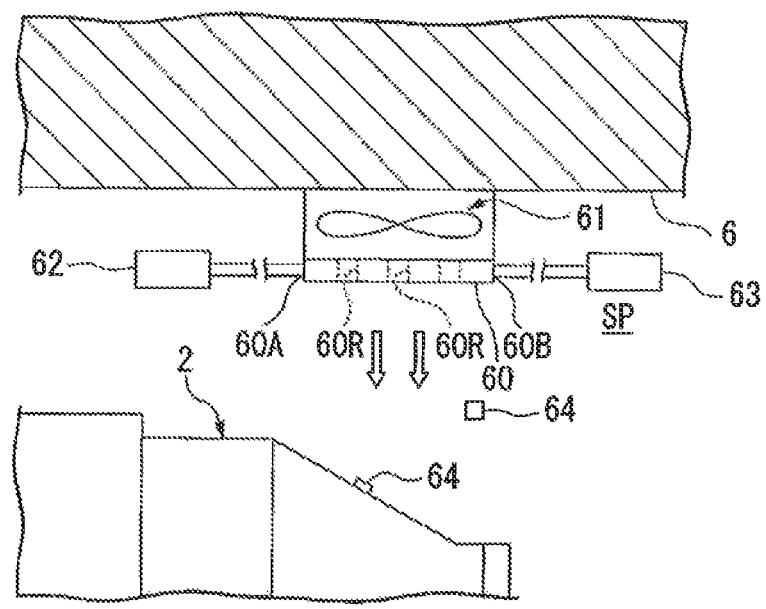
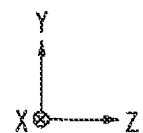

Fig. 14
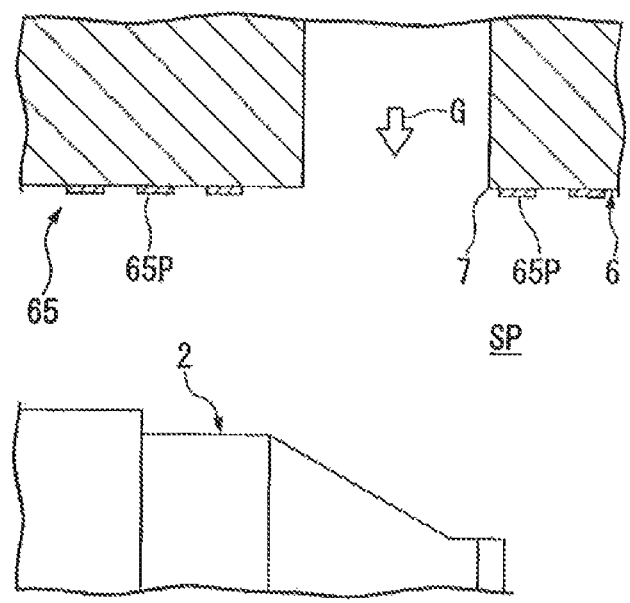
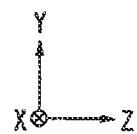

Fig. 15
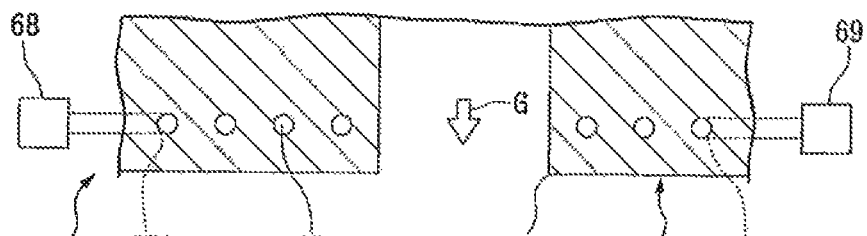
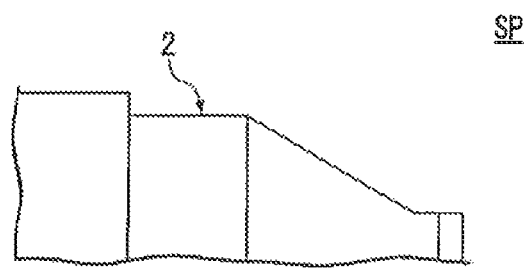
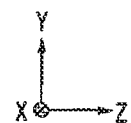

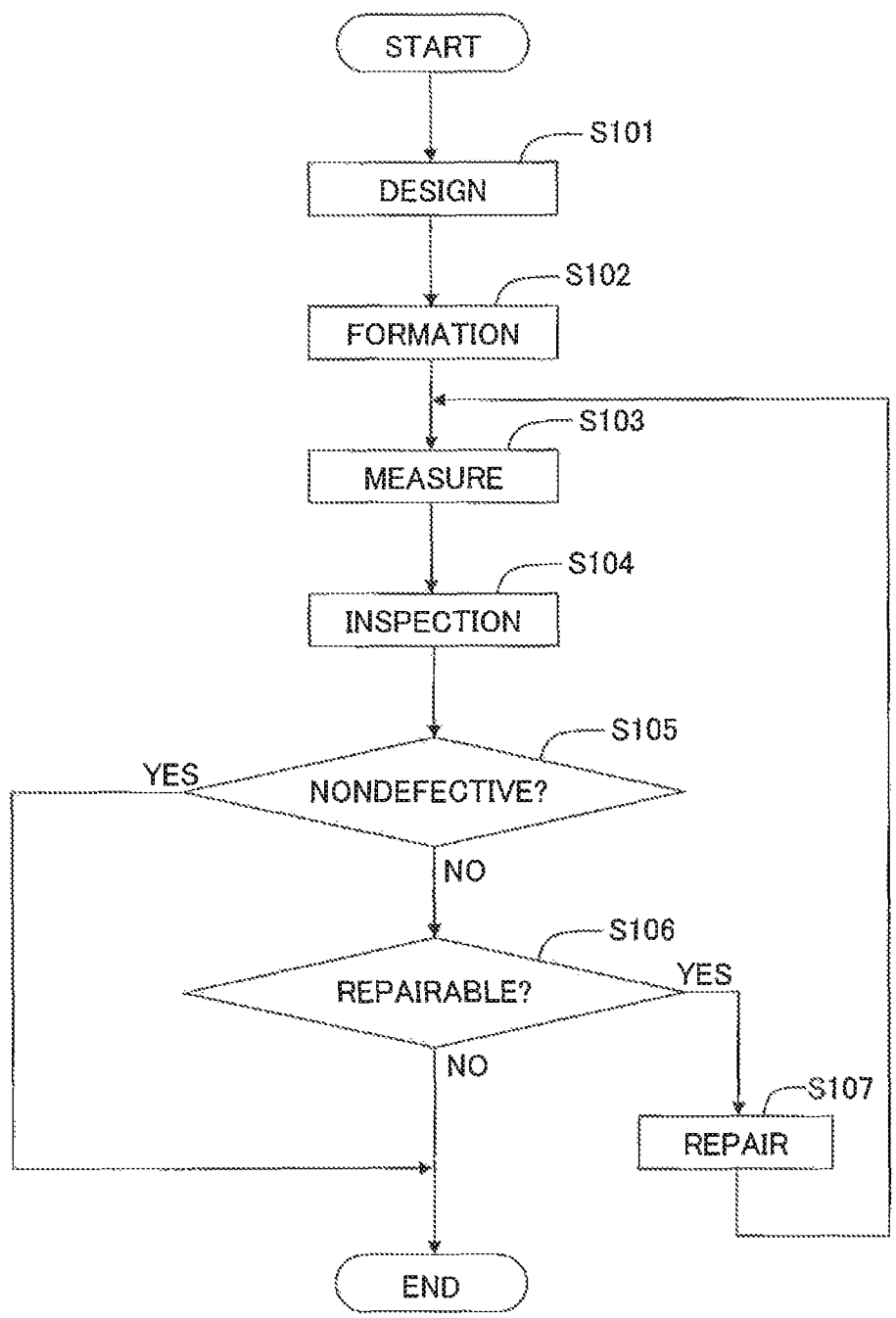

APPARATUS, X-RAY IRRADIATION METHOD, AND STRUCTURE MANUFACTURING METHOD

CROSS-REFERENCE TO RELATED APPLICATIONS

The present application claims priority from U.S. Provisional Patent Application No. 61/548,499 filed on Oct. 18, 2011 and claims priority from Japanese Patent Application No. 2011-220258 filed on Oct. 4, 2011, all the disclosures of which are incorporated herein by reference in their entirety.

BACKGROUND

1. Field of the Invention

The present invention relates to an apparatus, an X-ray irradiation method, and a structure manufacturing method.

2. Description of the Related Art

As apparatus nondestructively acquiring internal information of an object, for example, such apparatus as disclosed in the United States Patent Application Publication No 2009/0268869 is known to irradiate the object with X-ray and detect the transmission X-ray which has been transmitted through the object.

When temperature changes in a detection apparatus, it is possible for some members of the detection apparatus, for example, to be affected from thermal deformation. As a result, the detection accuracy can be decreased.

SUMMARY

An object of the present invention is to provide an apparatus, an X-ray irradiation method and a structure manufacturing method which are capable of restraining the decrease in detection accuracy.

According to an aspect of the present teaching, there is provided an apparatus configured to irradiate an object with an X-ray and detect a transmission X-ray transmitted through the object, including: a chamber member defining a first space; and a first supply port arranged in the first space to supply a temperature-controlled gas to a part of an X-ray source configured to irradiate the object with the X-ray.

BRIEF DESCRIPTION OF THE DRAWINGS

FIG. 10 is a view showing an example of a detection apparatus in accordance with a sixth embodiment;

FIG. 11 is a view showing an example of a detection apparatus in accordance with a seventh embodiment;

FIG. 13 is a view showing an example of a detection apparatus in accordance with a ninth embodiment;

FIG. 14 is a view showing an example of a detection apparatus in accordance with a tenth embodiment;

FIG. 15 is a view showing an example of a detection apparatus in accordance with an eleventh embodiment;

FIG. 20 is a flowchart showing a processing flow in the structural object manufacturing system.

DESCRIPTION OF THE EMBODIMENTS

While embodiments of the present teaching will be explained hereinbelow in reference to the accompanying drawings, the present teaching is not limited to the embodiments. In the following explanations, an X-Y-Z orthogonal coordinate system is set up, and positional relations between respective parts are explained in reference to this X-Y-Z orthogonal coordinate system. A predetermined direction in a horizontal plane is defined as a Z-axis direction, a direction orthogonal to the Z-axis direction in the horizontal plane is defined as an X-axis direction, and a direction orthogonal respectively to the Z-axis direction and the X-axis direction (i.e. a vertical direction) is defined as a Y-axis direction. Further, the rotational (inclinational) directions about the X-axis the Y-axis and the Z-axis are defined as a θX direction, a θY direction and a θZ direction, respectively.

<First Embodiment>

Figure 1:
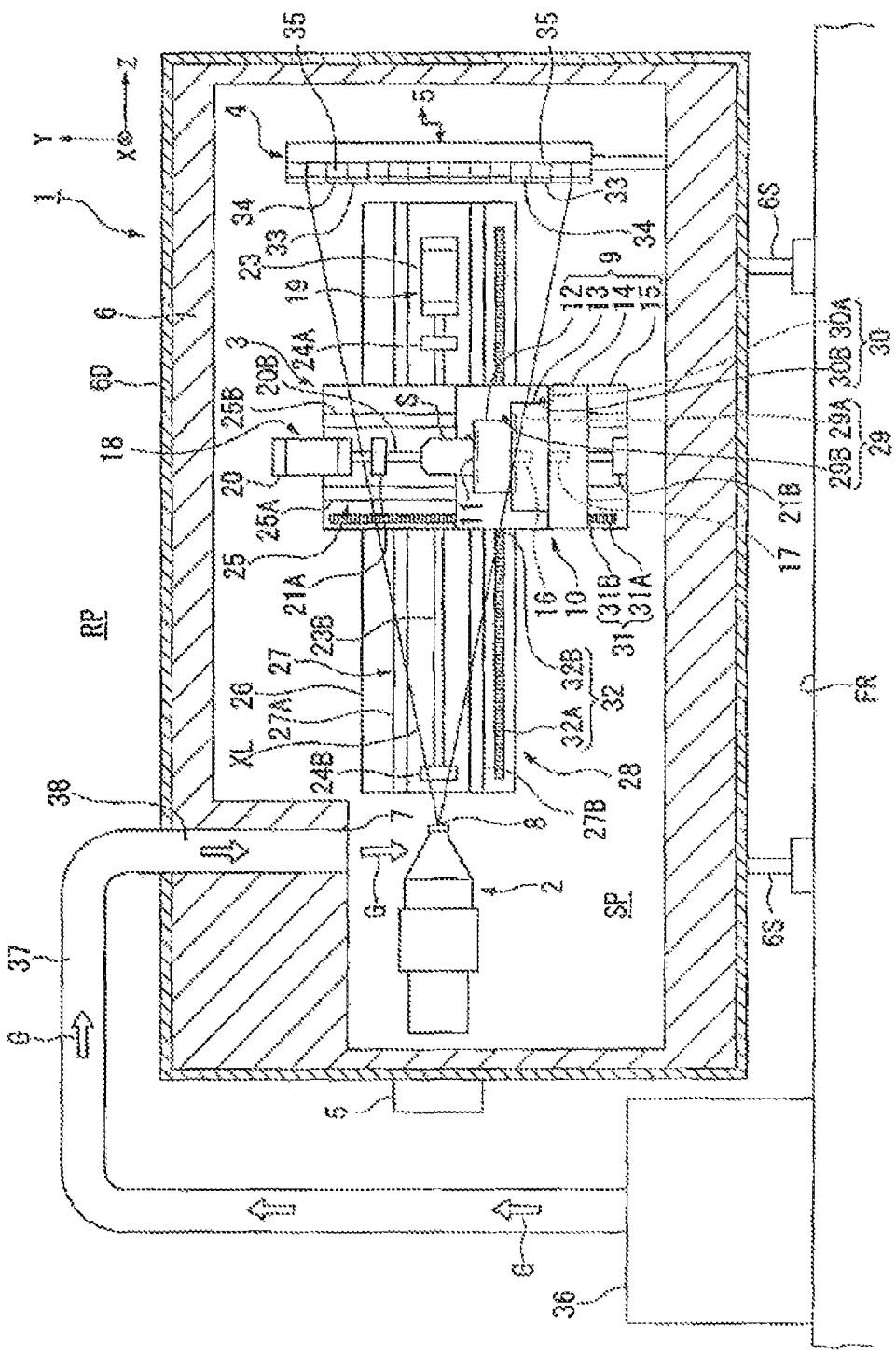
FIG. 1 is a view showing an example of a detection apparatus in accordance with a first embodiment.

A first embodiment will be explained. FIG. 1 is a view showing an example of a detection apparatus 1 in accordance with the first embodiment.

The detection apparatus 1 irradiates a measuring object S with an X-ray XL to detect a transmission X-ray transmitted through the measuring object S. The X-ray is, for example, an electromagnetic wave with a wavelength of approximately 1 pm to 30 nm. The X-ray includes at least one of an ultrasoft X-ray with energy of approximately 50 eV, a soft X-ray with energy of approximately 0.1 to 2 key, an X-ray with energy of approximately 2 to 20 keV, and a hard X-ray with energy of approximately 20 to 100 keV.

In the first embodiment, the detection apparatus 1 includes an X-ray CT detection apparatus irradiating the measuring object S with the X-ray and detecting the transmission X-ray transmitted through the measuring object S, so as to nondestructively acquire internal information of the measuring object S (the internal structure, for example). In the first embodiment, the measuring object S includes components for industrial use such as machine components, electronic components, and the like. The X-ray CT detection apparatus includes industrial X-ray CT detection apparatuses configured to irradiate the components for industrial use with the X-ray to inspect the components for industrial use.

In FIG. 1, the detection apparatus 1 includes an X-ray source 2 emitting the X-ray XL, a movable stage device 3 retaining the measuring object S, a detector 4 detecting the transmission X-ray transmitted through the measuring object S retained by the stage device 3, and a control device 5 controlling the operation of the entire detection apparatus 1.

Further, in the first embodiment, the detection apparatus 1 includes a chamber member 6 defining an internal space SP in which the X-ray XL emitted from the X-ray source 2 proceeds. In the first embodiment, the X-ray source 2, stage device 3, and detector 4 are arranged in the internal space SP.

Further, in the first embodiment, the detection apparatus 1 includes a supply port 7 supplying a temperature-control led gas G to at least part of the X-ray source 2. The supply port 7 is arranged in the internal space SP.

In the first embodiment, the chapter member 6 is arranged on a support surface FR. The support surface FP, includes floor surfaces in a factory or the like. The chamber member 6 is supported by a plurality of support members 6S. The chamber member 6 is arranged on the support surface FR via, the support members 6S. In the first embodiment, the support members 6S separate the lower surface of the chamber member 6 from the support surface FR. That is, an inter space is formed between the lower surface of the chamber member 6 and the support surface FR. Further, it is also possible for at least part of the lower surface of the chamber member 6 to contact with the support surface FR.

The first embodiment, the chamber member 6 contains lead. The chamber member 6 restrains the X-ray XL in the internal space SP from leaking out into an external space RP of the chamber member 6.

In the first embodiment, the detection apparatus 1 is installed in the chamber member 6, and has a member 6D with a lower thermal conductivity than that of the chamber member 6. In the first embodiment, the member 6D is arranged on the external surface of the chamber member 6. The member 6D restrains the temperature in the internal space SP from being affected by the temperature (change in temperature) in the external space RP. That is the member 6D functions as a thermal insulation member restraining the heat in the external space RP from transferring into the internal space SP. The member 6D contains such as plastic. In the first embodiment, the member 6D contains such as foamed polystyrene.

The X-ray source 2 irradiates the measuring object S with the X-ray XL. The X-ray source 2 has an emission portion 8 emitting the X-ray XL. The X-ray source 2 constitutes a point X-ray source. In the first embodiment, the emission portion 8 includes the point X-ray source. The X-ray source 2 irradiates the measuring object S with a conical X-ray (a so-called cone beam). Further, it is possible that the X-ray source 2 is capable of adjusting the intensity of the emitting X-ray XL. Adjusting the intensity of the X-ray XL emitted from the X-ray source 2 can be based on the X-ray absorption feature and the like of the measuring object S. Further, the spreading shape of the X-ray emitted from the X-ray source 2 is not limited to a cone. For example, the X-ray can alternatively be fan-like (a so-called fan beam).

The emission portion 8 is directed toward the +Z direction. In the first embodiment, at least part of the X-ray XL emitted from the emmission portion 8 proceeds in the +Z direction in the internal space SP.

The stage device 3 includes a movable stage 9 retaining the measuring object S, and a drive system 10 moving the stage 9.

In the first embodiment, the stage 9 has a table 12 having a retaining portion 11 retaining the measuring object S, a first movable member 13 movably supporting the table 12, a second movable member 14 movably supporting the first movable member 13, and a third movable member 15 movably supporting the second movable member 14.

The table 12 is rotatable in a state of retaining the measuring object S on the retaining portion 11. The table 12 is movable (rotatable) in the θY direction. The first movable member 13 is movable in the X-axis direction. If the first movable member 13 moves in the X-axis direction, then along with the first movable member 13, the table 12 also moves in the X-axis direction. The second movable member 14 is movable in the Y-axis direction. When the second movable member 14 moves in the Y-axis direction, then along with the second movable member 14, the first movable member 13 and the table 12 also move in the Y-axis direction. The third movable member 15 is movable in the Z-axis direction. When the third movable member 15 moves in the Z-axis direction, then along with the third movable member 15, the second movable member 14, the first movable member 13, and the table 12 also move in the Z-axis direction.

In the first embodiment the drive system 10 includes a rotary drive device 16 rotating the table 12 on the first movable member 13, a first drive device 17 moving the first movable member 13 on the second movable member 14 in the X-axis direction, a second drive device 18 moving the second movable member 14 in the Y-axis direction, and a third drive device 19 moving the third movable member 15 in the Z-axis direction.

The second drive device 18 includes a screw shaft 20B arranged in a not of the second movable member 14, and an actuator 20 rotating the screw shaft 20B. The screw shaft 20B is rotatably supported by bearings 21A and 21B. In the first embodiment, the screw shaft 20B is supported by the bearings 21A and 21B such that the shaft line of the screw shaft 20B becomes substantially parallel to the Y-axis. In the first embodiment, a ball is arranged between the screw shaft 20B and the nut of the second movable member 14. That is, the second drive device 18 includes a so-called ball screw drive mechanism.

The third drive device 19 includes a screw shaft 23B arranged in a nut of the third movable member 15, and an actuator 23 rotating the screw shaft 23B. The screw shaft 23B is rotatably supported by bearings 24A and 24B. In the first embodiment, the screw shaft 23B is supported by the bearings 24A and 24B such that the shaft line of the screw shaft 23B becomes substantially parallel to the Z-axis. In the first embodiment, a ball is arranged between the screw shaft 23B and the nut of the third movable member 15. That is the third drive device 19 includes a so-called ball screw drive mechanism.

The third movable member 15 has a guide mechanism 25 guiding the second movable member 14 in the Y-axis. The guide mechanism 25 includes guide members 25A and 25B elongated in the Y-axis. The third movable member 15 supports at least part of the second drive device 18 including the actuator 20, and the bearings 21A and 21B supporting the screw shaft 20B. By letting the actuator 20 rotate the screw shaft 20B, the second movable member 14 moves in the Y-axis direction while being guided by the guide mechanism 25.

In the first embodiment, the detection apparatus 1 has a base member 26. The base member 26 is supported by the chamber member 6. In the first embodiment, the base member 26 is supported by the inner wall (inner surface) of the chamber member 6 via a support mechanism. The base member 26 is fixed at a predetermined position.

The base member 26 has a guide mechanism 27 guiding the third movable member 15 in the Z-axis. The guide mechanism 27 includes guide members 27A and 27B elongated in the Z-axis. The base member 26 supports at least part of the third drive device 19 including the actuator 23, and the bearings 24A and 24B supporting the screw shaft 23B. By letting the actuator 23 rotate the screw shaft 23B, the third movable member 15 moves in the Z-axis direction while being guided by the guide mechanism 27.

Further, while illustration is omitted, the second movable member 14 has a guide mechanism guiding the first movable member 13 in the X-axis direction in the first embodiment. The first drive device 17 includes a ball screw mechanism capable of moving the first movable member 13 in the X-axis direction. The rotary drive device 16 includes a motor capable of moving (rotating) the table 12 in the θY direction.

In the first embodiment, the measuring object S retained on the table 12 is movable in four directions, i.e. the X-axis, Y-axis, Z-axis and θY directions, by the drive system 10. Further, it is also possible for the drive system 10 to move the measuring object S retained on the table 12 in six directions, i.e. the X-axis, Y-axis, Z-axis, θX, θY and θZ directions. Further, in the first embodiment, although the drive system 10 is supposed to include a ball screw drive mechanism, it can alternatively include, for example, a voice coil motor. Still alternatively, the drive system 10 can include, for example, a linear motor or a planar motor.

In the first embodiment, the stage 9 is movable in the internal space SP. The stage 9 is arranged on the +Z side of the emission portion 8. The stage 9 is movable in the space on the +Z side from the emission portion 8 within the internal space SP. At least a part of the stage 9 can face the emission portion 8. The stage 9 can set the retained measuring object S to is position facing the emission portion 8. The stage 9 can set the measuring object S in the path through which the X-ray XL emitted from the emission portion 8 is transmitted. The stage 9 can be arranged within the irradiation area of the X-ray XL emitted from the emission portion 8.

In the first embodiment, the detection apparatus 1 includes a measuring system 28 measuring the position of the stage 9. In the first embodiment, the measuring system 28 includes an encoder system.

The measuring system 28 has a rotary encoder 29 measuring the rotational amount of the table 12 (the position with respect to the θY direction), a linear encoder 30 measuring the position of the first movable member 13 with respect to the X-axis direction, another linear encoder 31 measuring the position of second movable member 14 with respect to the Y-axis direction, and still another linear encoder 32 measuring the position of third movable member 15 with respect to the Z-axis direction.

In the first embodiment, the rotary encoder 29 measures the rotational amount of the able 12 relative, to the first movable member 13. The linear encoder 30 measures the position of the first movable member 13 (the position with respect to the X-axis direction) relative to the second movable member 14. The linear encoder 31 measures the position of the second movable member 14 (the position with respect to the Y-axis direction) relative to the third movable member 15. The linear encoder 32 measures the position of the third movable member 15 (the position with respect to the Z-axis direction) relative to the base member 26.

The rotary encoder 29 includes, for example, a scale member 29A arranged on the fit movable member 13, and an encoder head 29B arranged on the table 12 to detect the calibrations of the scale member 29A. The scale member 29A is fixed on the first movable member 13. The encoder head 29B is fixed on the table 12. The encoder head 29B can measure the rotational amount of the table 12 relative to the scale member 29A (the first movable member 13).

The linear encoder 30 includes, for example, a scale member 30A arranged on the second movable member 14, and an encoder head 30B arranged on the first movable member 13 to detect the calibrations of the scale member 30A. The scale member 30A is fixed on the second movable member 14. The encoder head 30B is fixed on the first movable member 13. The encoder head 30B can measure the position of the first movable member 13 relative to the scale member 30A (the second movable member 14).

The linear encoder 31 includes a scale member 31A arranged on the third movable member 15, and an encoder head 31B arranged on the second movable member 14 to detect the calibrations of the scale member 31A. The scale member 31A is fixed on the third movable member 15. The encoder head 31B is fixed on the second movable member 14. The encoder head 31B can measure the position of the second movable member 14 relative to the scale member 31A (the third movable member 15).

The linear encoder 32 includes a scale member 32A arranged on the base member 26, and an encoder head 32B arranged on the third movable member 15 to detect the calibrations of the scale member 32A. The scale member 32A is fixed on the base member 26. The encoder head 32B is fixed on the third movable member 15. The encoder head 32B can measure the position of the third movable member 15 relative to the scale member 32A (the base member 26).

The detector 4 is arranged on the +Z side from the X-ray source 2 and the stage 9. The detector 4 is fixed at a predetermined position. Further, it is also possible for the detector 4 to be movable. The stage 9 is movable in the space between the X-ray source 2 and the detector 4 within the internal space SP.

The detector 4 has scintillator portions 34 having an incidence surface 33 on which the X-ray XL enters, the X-ray XL coming from the X-ray source 1 and including the transmission ray transmitted through the measuring object S; and light-receiving portions 35 respectively receiving the light generated in the scintillator portions 34. The incidence surface 33 of the detector 4 can face the measuring object S retained on the stage 9.

Each of the scintillator portions 34 includes a scintillation substance which generates a light with a wavelength different from that of the X-ray, by exposing itself to an X-ray. Each of the light-receiving portions 35 includes a photomultiplier tube. The photomultiplier tube includes a phototube converting optical energy into electrical energy by photoelectric effect. The light-receiving portions 35 amplify a weak electric signal arising from the light generated in the scintillator portions 34. That is, the light-receiving portions 35 convert the light generated in the scintillator portions 34 into the electrical signal and output the same.

The detector 4 has a plurality of the scintillator portions 34. The plurality of scintillator portions 34 are arranged in the X-Y plane. The scintillator portions 34 are arranged in an array-like form. The detector 4 has a plurality of the light-receiving portions 35 to connect respectively with the plurality of scintillator portions 34. Further, it is also possible for the detector 4 to directly convert the incident X-ray into the electrical signal without converting the incident X-ray into the light. In other words, the detector 4 is not necessarily limited to using a scintillation detector having the scintillator portions 34, but can use other types of X-ray detectors. For example, it is also possible to use detectors directly converting the incident X-ray into the electrical signal without converting the incident X-ray into the light, such as semiconductor detectors (e.g. silicon detectors and the like), and gas detectors (e.g. ionization chambers and the like).

The supply port 7 supplies the temperature-controlled gas G to at least part of the X-ray source 2. In the first embodiment, the detection apparatus 1 includes an adjusting device 36 controlling or adjusting the temperature of the gas G. The adjusting device 36 operates on such as electric power. The supply port 7 supplies the internal space SP with the gas G from the adjusting device 36.

In the first embodiment, the adjusting device 36 is arranged in the external space RP of the chamber member 6. In the first embodiment, the adjusting device 36 is arranged on the support surface FR. The adjusting device 36 is connected with a duct 37. The duct 37 is also arranged in the external space RP. The adjusting device 36 is separate from the chamber member 6. At least part of the duct 37 is separate from the chamber member 6.

The chamber member 6 has a duct 38. The duct 38 is formed to link the internal space SP and the external space RP. The opening at one end of the duct 38 is arranged to front on the external space RP. The opening at the other end of the duct 38 is arranged to front on the internal space SP. The flow passage of the duct 38 is connected with the opening at the one end of the duct 38. In the first embodiment, the opening at the other end of the duct 38 functions as the supply port 7.

In the first embodiment the adjusting device 36 takes in some gas in the external space RP, for example, to control or regulate the temperature of the gas. The gas G temperature-controlled by the adjusting device 36 is sent to the supply port 7 via the flow passage of the duct 37, and the duct 38 of the chamber member 6. The supply port 7 is arranged to face at least part of the X-ray source 2. The supply port 7 supplies at least part of the X-ray source 2 with the gas G from the adjusting device 36. Further, the duct 37 and the duct 38 can be integrated into one body, or at least part of the duct 37 and at least part of the duct 38 can be different members from each other.

Figure 2:
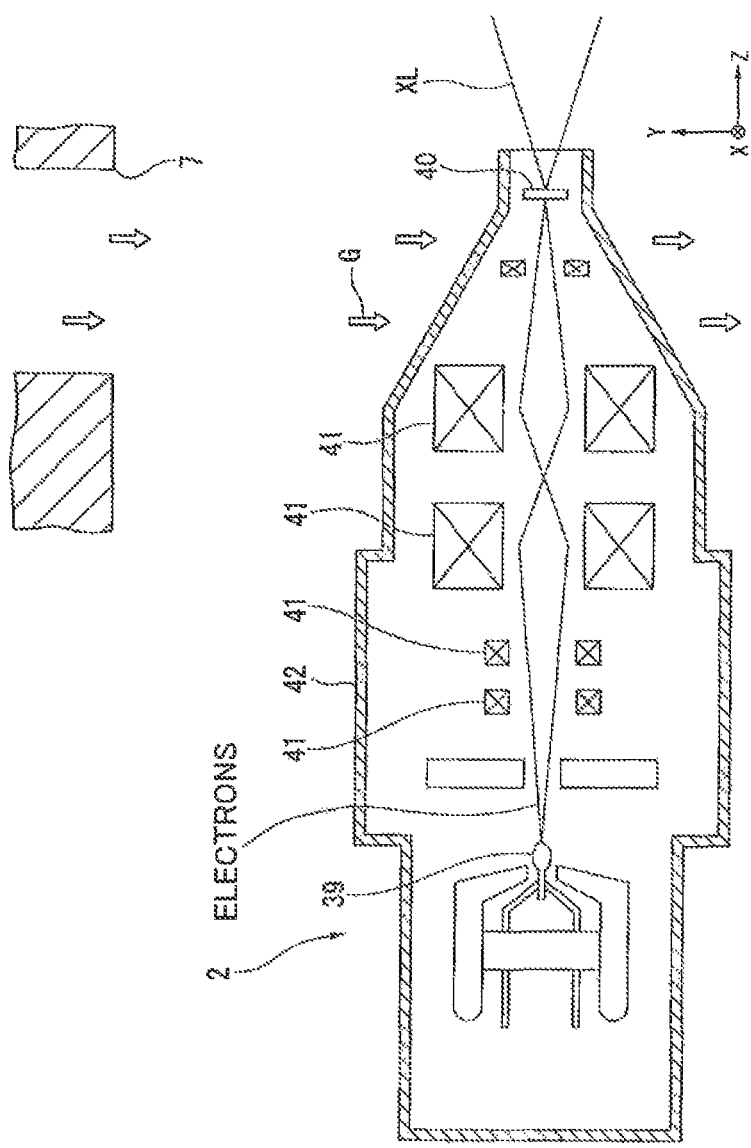
FIG. 2 is a view showing an example of an X-ray source in accordance with the first embodiment.

FIG. 2 is a cross-sectional view showing an example of the X-ray source 2 in accordance with the first embodiment. In FIG. 2, the X-ray source 2 includes a filament 39 generating electrons, a target 40 generating an X-ray by collision of the electrons or transmission of the electrons, and electron conduction members 41 conducting the electrons to the target 40. Further, in the first embodiment, the X-ray source 4 includes a housing 42 accommodating at least some of the electron conduction members 41. In the first embodiment, the housing 42 accommodates all of the filament 39, the electron conduction members 41, and the target 40.

The filament 39 contains such as tungsten. When an electric current flows through the filament 39 and the filament 39 is heated by the electric current, electrons (thermoelectrons) are emitted from the filament 39. The filament 39 is shaped with a pointed apical end, from which the electrons are easy to be emitted. The filament 39 is shaped as has been wound into a coil. Further, the supply source of the electrons (thermoelectrons) in the X-ray source 2 is not necessarily limited to a filament. For example, it is also possible to use an electron gun.

The target 40 contains such as tungsten to generate the X-ray by collision of the electrons or transmission of the electrons. In the first embodiment, the X-ray source 2 is a so-called transmission type. In the first embodiment, the target 40 generates the X-ray by transmission of the electrons.

For example, with the target 40 as the anode and the filament 39 as the cathode, when a voltage is applied between the target 40 and the filament 39, then the thermoelectrons emitted from the filament 39 will accelerate toward the target 40 (anode) to irradiate the target 40. By virtue of this, the X-ray is generated from the target 40.

The electron conduction members 41 are arranged in at least part of the periphery (surrounding) of the pathway of the electrons from the filament 39 between the filament 39 and the target 40. Each of the electron conduction members 41 includes, for example, an electron lens such as a focusing lens and an object lens and the like, or a polariscope, to conduct the electrons from the filament 39 to the target 40. The electron conduction members 41 cause the electrons to collide against some area of the target 40 (focal point of the X-ray). The dimension of the area (the spot size) in the target 40 against which the electrons collide is sufficiently small. By virtue of this, a substantial point X-ray source is formed.

In the first embodiment, the temperature-controlled gas G is supplied from the supply port 7 to the external surface of the housing 42. In the first embodiment, the supply port 7 faces at least part of the external surface of the housing 42. In the first embodiment, the supply port 7 is arranged above (on the +Y side of) the X-ray source 2 (the housing 42). The supply port 7 causes the gas G to blow from above the X-ray source 2 onto the external surface of the housing 42 of the X-ray source 2.

In the X-ray source 2, when the target 40 is irradiated with the electrons, then some energy of the electrons becomes X-ray while some energy of the electrons becomes heat. Irradiating the target 40 with the electrons causes an increase in the temperatures of the space surrounding the target 40 and of the members arranged in the vicinity of the target 40.

When the temperature of the target 40 increases, then it is possible that, for example, the target 40 and/or the housing 42 undergo(es) thermal deformation, and/or the relative position between the filament 39 and target 40 undergoes a change. Further, when the temperature of the X-ray source 2 including the target 40 increases, then it is possible to bring about a temperature change in the internal space SP where the X-ray source 2 is placed. Further, when the temperature of the X-ray source 2 including the target 40 increases, then it is possible that, for example, the guide member 26 and/or the detector 4 undergo(es) thermal deformation, and/or deformation occurs in at least part of the stage device 3 including the stage 9 and the drive system 10. Further, when the temperature of the X-ray source 2 increases, then it is possible that, for example, the relative position between the X-ray source 2 and stage 9 undergoes a change, the relative position between the X-ray source 2 and detector 4 undergoes a change, and/or the relative position between the stage 9 and detector 4 undergoes a change. In this manner, when the temperature of the X-ray source 2 changes, then it is possible that thermal deformation occurs in at least some members of the detection apparatus 1, and/or the relative position between some members undergoes a change. As a result, it is possible to decrease the detection accuracy (inspection accuracy; measurement accuracy) of the detection apparatus 1.

In the first embodiment, because the temperature-controlled gas G is supplied to at least part of the X-ray source 2 producing heat, it is realized to restrain the thermal deformation in at least some members including the X-ray source 2 in the internal space SP, the temperature change in the internal space SP, and/or the change in relative position between some members in the internal space SP.

Further, in the first embodiment while a plurality of members including the X-ray source 2 the stage 9, the detector 4 and the like are arranged in the internal space SP, the temperature-controlled gas G is supplied to at least part of the X-ray source 2 producing heat among those multiple members. Therefore, in the internal space SP, the X-ray source 2 has the highest arrival ratio of the temperature-controlled gas G among the plurality of members including the X-ray source 2, the stage 9, the detector 4, and the like. Further, in the first embodiment, while the plurality of members including the X-ray source 2, the stage 9, the detector 4 and the like are arranged in the internal space SP, the temperature-controlled gas G is supplied to part of the X-ray source 2. In the first embodiment, it is possible to control the temperature surrounding the X-ray source 2 in a local space smaller than the internal space SP within the internal space SP. Further, while the plurality of members including the X-ray source 2, the stage 9, the detector 4 and the like are arranged in the internal space SP, it is possible to control the temperature of only the part of the X-ray source 2 reached by the temperature-controlled gas G without supplying the temperature-controlled gas G to all of the multiple members.

Next, explanations will be made with respect to an example of operation of the detection apparatus in accordance with the first embodiment.

Figure 3:
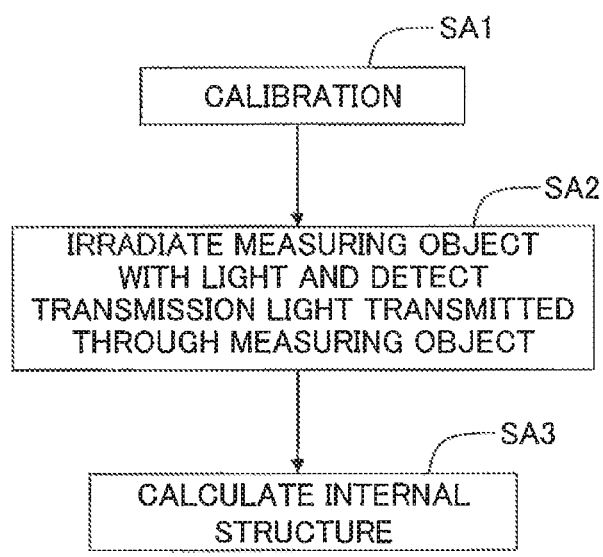
FIG. 3 is a flowchart for explaining an example of operation of the detection apparatus in accordance with the first embodiment.

In the first embodiment, as shown in the flowchart of FIG. 3, such steps are carried out as calibrating the detection apparatus 1 (step SA1), irradiating the measuring object S with the X-ray XL and detecting the transmission X-ray transmitted through the measuring object S (step SA2), and calculating the internal structure of the measuring object S (step SA3).

Figure 4:
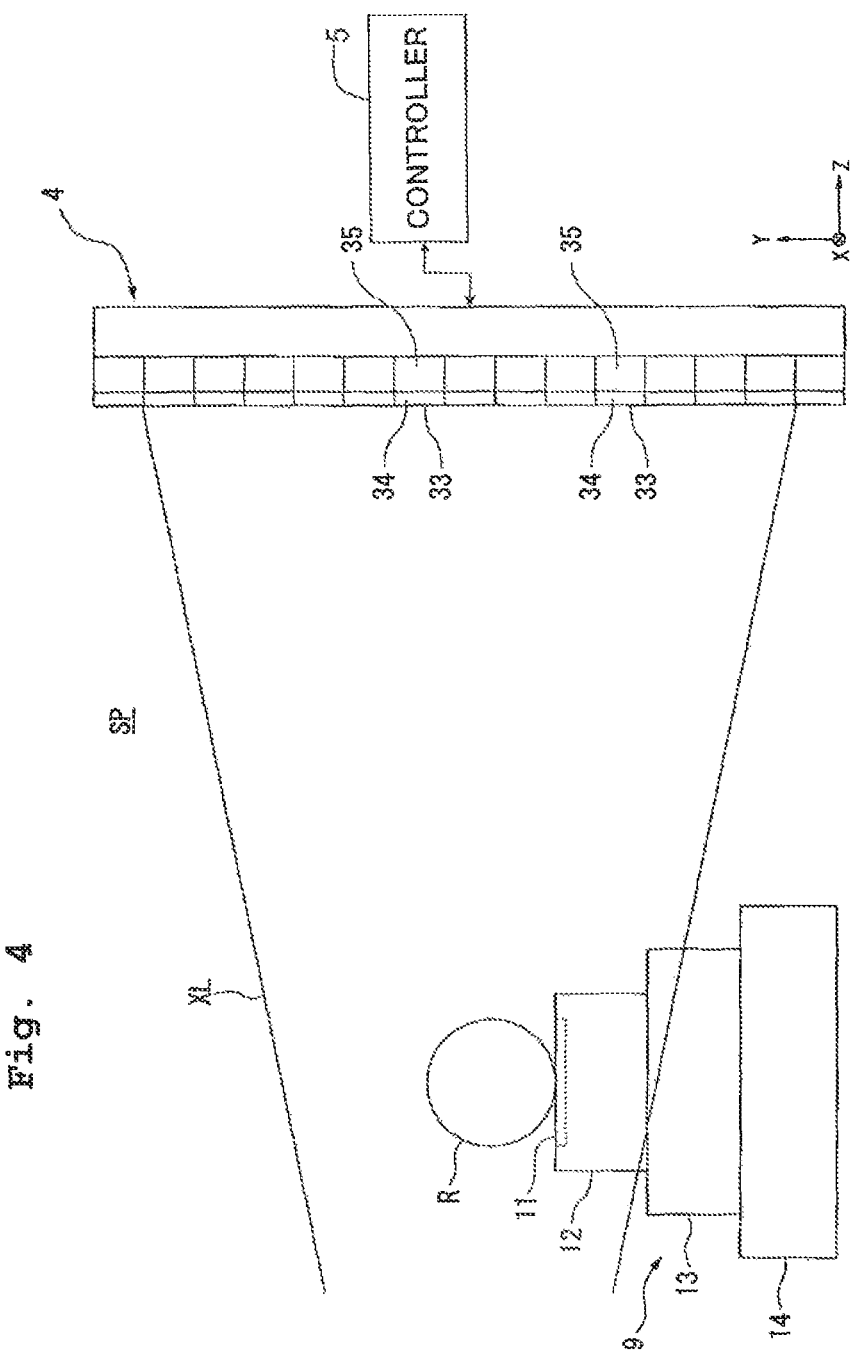
FIG. 4 is a view for explaining the example of operation of the detection apparatus in accordance with the first embodiment.

First, the calibration (step SA1) will be explained. FIG. 4 is a schematic view showing an example of calibration in accordance with the first embodiment. As shown in FIG. 4, in the calibration, a reference member R different from the measuring object S is retained on the table 12. Further, in the calibration, the temperature-controlled gas G is supplied from the supply port 7 to at least part of the X-ray source 2. By supplying the temperature-controlled gas G from the supply port 7 to the X-ray source 2, the temperature in the internal space SP containing the X-ray source 2 is controlled with the gas G.

In the following explanations, a predetermined temperature Ta is used as appropriate to refer to the temperature in the internal space SP containing the X-ray source 2, which has been controlled with the gas G supplied from the supply port 7.

As shown in FIG. 4, in the first embodiment, the reference member R is a spherical object. The profile (dimension) of the reference member R is known. The reference member R is an object restrained from thermal deformation. The reference member R is an object which is restrained from thermal deformation at least to a greater degree than the measuring object S. Even if a temperature change occurs in the internal space SP, the profile (dimension) of the reference member R virtually does not change. Further, in the first embodiment, the reference member R is not limited to a spherical shape.

The control device 5 measures the position of the stage 9 with the measuring system 28 while controlling the drive system 10 to adjust the position of the stage 9 retaining the reference member R. The control device 5 adjusts the position of the stage 9 such that the reference member R can be disposed at a reference position Pr.

Along with at least part of the supply of the gas G from the supply port 7, the control device 5 causes an electric current to flow through the filament 39 for emitting X-ray from the X-ray source 2. By virtue of this, the filament 39 is heated, and thereby electrons are emitted from the filament 39. The target 40 is then irradiated with the electrons emitted from the filament 39. By virtue of this, X-ray is generated from the target 40.

The reference member R is irradiated with the X-ray XL generated from the X-ray source 2. At the predetermined temperature Ta, when the reference member R is irradiated with the X-ray XL from the X-ray source 2, then the X-ray XL irradiating the reference member R is transmitted through the reference member R. The transmission X-ray transmitted through the reference member R then falls on the incidence surface 33 of the detector 4. The detector 4 detects the transmission X-ray transmitted through the reference member R. At the predetermined temperature Ta, the detector 4 detects an image of the reference member R obtained based on the transmission X-ray transmitted through the reference member R. In the first embodiment, the dimension (size) of the image of the reference member R obtained at the predetermined temperature Ta is referred to as a dimension Wa. The detection result from the detector 4 is outputted to the control device 5.

Based on the dimension of the image of the reference member R and the dimension of the reference member R, the control device 5 calculates the relative positions between the X-ray source 2, the reference member R and the detector 4. Further, although one spherical object is used in the first embodiment, it is also possible to use a plurality of spherical objects. When a plurality of spherical objects are used, then the positions of the spherical objects can differ from each other, for example, in one or both of the Y-axis direction and the Z-axis direction. Further, when a plurality of spherical objects are used, then the relative positions between the X-ray source 2, the reference members R and the detector 4 can be calculated not based on the images of the reference members R but based on the distances between the respective reference members R. Further, the distances between the respective reference members R can be calculated either as the distances between the central positions of the respective reference members R or as the distances between predetermined profile positions of the respective reference members R.

In the first embodiment, a change in the temperature T of the internal space SP causes a change in the dimension (size) of the image obtained based on the transmission X-ray. Further, the dimension of the image obtained based on the transmission X-ray is the dimension of the image acquired by the detector 4, including, for example, the dimension of the image formed in the incidence surface 33.

For example, when the temperature T changes, then a variation or a fluctuation occurs in the relative positions between the X-ray source 2, the reference member R, and the detector 4 (the relative positions in the Z-axis direction). For example, when the internal space SP is at a reference temperature Tr (ideal temperature; target temperature), then a reference dimension Wr is used to refer to the dimension of the image acquired by the detector 4 based on the X-ray XL used to irradiate the reference member R disposed at the reference position Pr.

On the other hand, when the internal space SP is at a temperature TX different from the reference temperature Tr, then it is possible to give rise to thermal deformation in, for example, at least some of the X-ray source 2, stage 9, detector 4, base member 26 (scale member 32A) and chamber member 6, thereby altering the relative positions between the X-ray source 2, the reference member R retained on the stage 9, and the detector 4. As a result, for example, even though the position of the stage 9 is adjusted based on the measuring result from the measuring system 28 to dispose the reference member R at the reference position Pr, it is possible that the reference member R is not actually disposed at the reference position Pr. In other words, when the internal space SP is at the temperature TX, it is possible that the reference member R is disposed at a position PX different from the reference position Pr. Further, the position PX includes the relative position of the reference member R with respect to at least one of the X-ray source 2 and the detector 4.

Further, when a variation occurs in the relative positions between the X-ray source 2, the reference member R and the detector 4 with the internal space SP at the temperature TX, then the dimension WX of the image acquired by the detector 4 is different from the reference dimension Wr.

In the first embodiment, the control device 5 includes a storage device. The storage device stores a relationship between the temperature T in the internal space SP, and the dimension (size) of the image of the reference member R obtained based on the transmission X-ray transmitted through the reference member R out of the X-ray XL irradiating the reference member R at the temperature T.

Further, as described above, along with the change of the temperature T in the internal space SP, a change occurs in the relative positions between the X-ray source 2, the reference member R, and the detector 4. Further, along with the change in the relative positions, a change occurs in the dimension of the image acquired by the detector 4. The storage device also stores a relationship between the relative positions and the image dimension.

Further, the information stored in the storage device is found through at least one of a preliminary experiment and a simulation.

Therefore, the control device 5 can calculate the relative positions between the X-ray source 2, the reference member R and the detector 4 at the temperature T based on the information stored in the storage device, and the image dimension of the reference member R acquired by the detector 4.

For example, when the internal space SP is at the predetermined temperature Ta, the control device 5 can calculate the relative positions between the X-ray source 2, the reference member B and the detector 4 at the predetermined temperature Ta based on the information stored in the storage device, and the image dimension Wa of the reference member R acquired by the detector 4.

Figure 5:
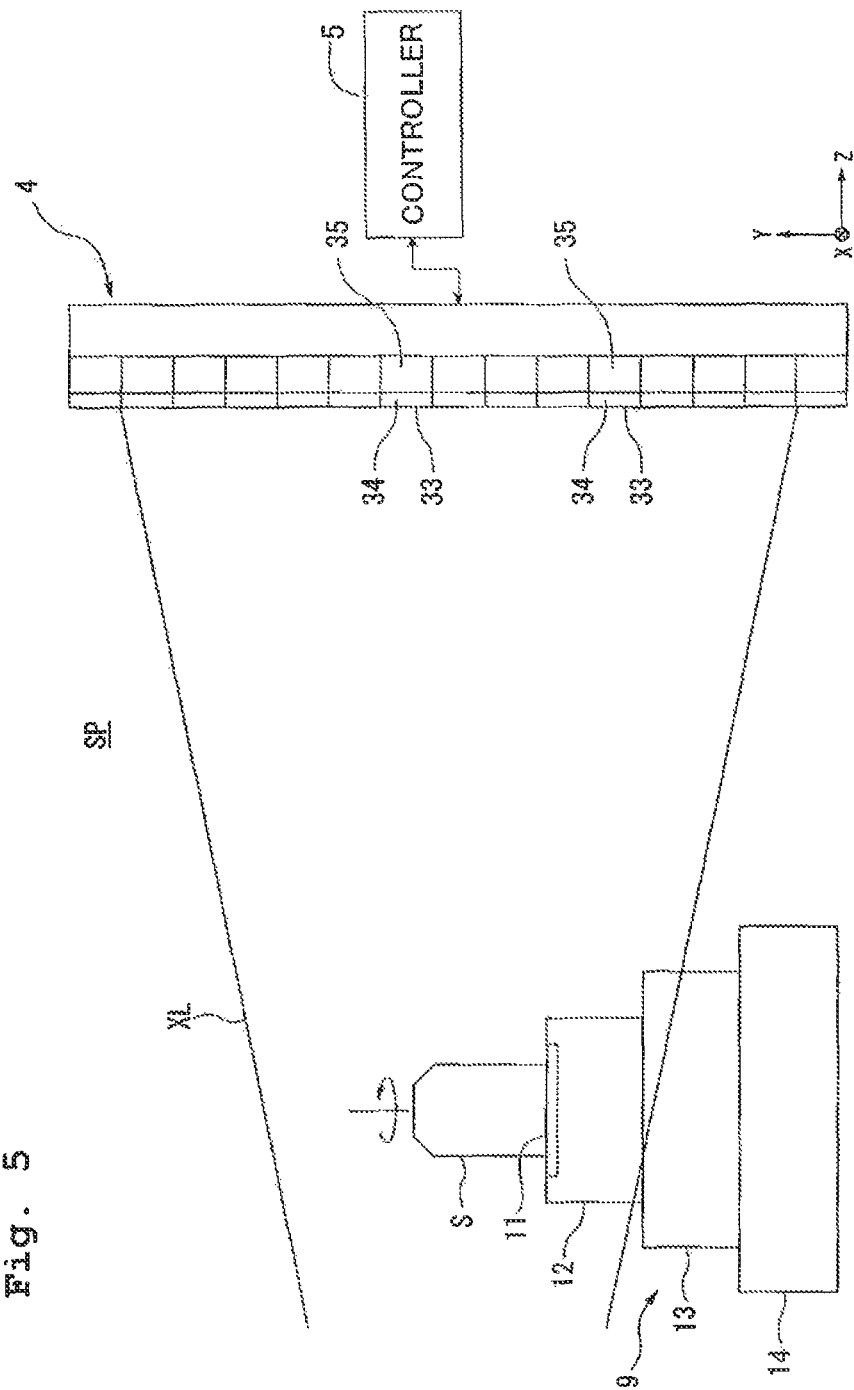
FIG. 5 is another view for explaining the example of operation of the detection apparatus in accordance with the first embodiment.

After the calibration is finished, detection of the measuring object S is carried out (step SA2). FIG. 5 is a schematic view showing an example of the detection in accordance with the first embodiment. As shown in FIG. 5, the measuring object S is retained on the table 12 in the detection. The control device 5 controls the stage device 3 to dispose the measuring object S between the X-ray source 2 and the detector 4.

Further in the detection, the temperature-controlled gas G is supplied from the supply port 7 to at least part of the X-ray source 2. By supplying the temperature-controlled gas G from the supply port 7 to the X-ray source 2 the temperature in the internal space SP containing the X-ray source 2 is controlled with the gas G.

The control device 5 causes the temperature-controlled gas G to be supplied from the supply port 7 to the internal space SP containing the X-ray source 2 such that the internal space SP is at the predetermined temperature Ta.

The control device 5 measures the position of the stage 9 with the measuring system 28 while controlling the drive system 10 to adjust the position of the stage 9 retaining the reference member R.

Along with at least part of the supply of the gas G from the supply port 7, the control device 5 causes an electric current to flow through the filament 39 for emitting X-ray from the X-ray source 2. By virtue of this, the filament 39 is heated, and thereby electrons are emitted from the filament 39. The target 40 is then irradiated with the electrons emitted from the filament 39. By virtue of this, X-ray is generated from the target 40.

The measuring object S is irradiated with at least part of the X-ray XL generated from the X-ray source 2. At the predetermined temperature Ta, when the measuring object S is irradiated with the X-ray XL from the X-ray source 2, then at least part of the X-ray XL irradiating the measuring object S is transmitted through the measuring object S. The transmission. X-ray transmitted through the measuring object S then enters on the incidence surface 33 of the detector 4. The detector 4 detects the transmission X-ray transmitted through the measuring object S. At the predetermined temperature Ta, the detector 4 detects an image of the measuring object S obtained based on the transmission X-ray transmitted through the measuring object S. In the first embodiment, the dimension (size) of the image of the measuring object S obtained at the predetermined temperature Ta is referred to as a dimension Ws. The detection result from the detector 4 is outputted to the control device 5.

In the first embodiment, the control device 5 uses the calibration result to correct the detection result of the transmission X-ray transmitted through the measuring object S out of the X-ray XL irradiating the measuring object S at the predetermined temperature Ta.

For example, the control device 5 corrects the image of the measuring object S obtained at the predetermined temperature Ta such that the image of the measuring object S obtained at the predetermined temperature Ta conforms to the image obtained at the reference temperature Tr.

For example, in the case of the dimension Ws of the image of the measuring object S obtained at the predetermined temperature Ta, the control device 5 multiplies the dimension Ws by a correction value Wr/Wa. That is, the control device 5 carries out the operation Ws×(Wr/Wa). By virtue of this, even when the actual temperature in the internal space SP is the predetermined temperature Ta, the control device 5 can still, calculate the image (image dimension) of the measuring object S at the reference temperature Tr.

In the first embodiment, in order to change the irradiation area of the measuring object S with the X-ray XL from the X-ray source 2, the control device 5 causes the X-ray XL from the X-ray source 2 to irradiate the measuring object S while changing the position of the measuring object S. That is, the control device 5 causes the X-ray XL from the X-ray source 2 to irradiate the measuring object S at each of multiple positions of the measuring object S, and lets the detector 4 detect the transmission X-ray transmitted through the measuring object S.

In the first embodiment, the control device 5 changes the irradiation area of the measuring object S with the X-ray XL front the X-ray source 2 by rotating the table 12 retaining the measuring object S to change the position of the measuring object S relative to the X-ray source 2.

That is, in the first embodiment, the control device 5 causes the X-ray XL to irradiate the measuring object S while rotating the table 12 retaining the measuring object S. The detector 4 detects the transmission. X-ray (X-ray transmission data) transmitted through the measuring object S at each position (each rotation angle) of the table 12. The detector 4 acquires an image of the measuring object S at each position.

The control device 5 calculates the internal structure of the measuring object from the detection result of the detector 4 (step SA3). In the first embodiment, the control device 5 acquires an image of the measuring object S based on the transmission X-ray (X-ray transmission data) transmitted through the measuring object S at each of the respective positions (each rotation angle) of the measuring object S. That is, the control device 5 acquires a plurality of images of the measuring object S.

The control device S carries out a calculational operation based on the plurality of X-ray transmission data (images) obtained by irradiating the measuring object S with the X-ray XL while rotating the measuring object S, to reconstruct a tomographic image of the measuring object S and acquire a three-dimensional data of the internal structure of the measuring object S (a three-dimensional structure). By virtue of this the internal structure of the measuring object S calculated. As a method for reconstructing a tomographic image of the measuring object, for example, the back projection method, the filtered back projection method, or the successive approximation can be adopted. With respect to the back projection method and the filtered back projection method, descriptions are given in, for example, U.S. Patent Application Publication No. 2002/0154728. Further, with respect to the successive approximation, a description is given in, for example, U.S. Patent Application Publication No. 2010/0220908. All the disclosures of these U.S. patent applications are incorporated herein by reference in their entirety.

As described above, according to the first embodiment, because the X-ray source 2 is supplied with the temperature-controlled gas G from the supply port 7, it is possible to control the temperature of the X-ray source 2. Therefore, it is possible to restrain at least part of the X-ray source 2 from thermal deformation. Further, by supplying the temperature-controlled gas G from the supply port 7, it is possible to control the temperature in the internal space SP, thereby making it possible to restrain the temperature in the internal space SP from variation.

Further, by supplying the temperature-controlled gas G from the supply port 7, temperature is controlled for at least some of the members disposed in the internal apace SP such as the stage device 3, the base member 26, the detector 4, and the like. Thereby, it is possible to restrain those members from thermal deformation. Further, by supplying the temperature-controlled gas G from the supply port 7, it is possible to restrain variation in the relative positions between, for example, the X-ray source 2, the measuring object S (the table 12), and the detector 4.

Therefore, it is possible to restrain decrease in the detection accuracy of the detection apparatus 1. For example, the detection apparatus 1 can accurately acquire information about the internal structure of the measuring object S.

Further, in the first embodiment, it is also possible for the control device 5 to let the X-ray source 2 be supplied with the temperature-controlled gas G from the supply port 7 at least when the X-ray source 2 is emitting the X-ray XL. In other words, the control device 5 can let the X-ray source 2 be supplied with the temperature-controlled gas G at least when the electric current is flowing through the filament 39. By virtue of this, temperature change is restrained, from occurring in the X-ray source 2, the internal space SP, and at least some of the members surrounding the X-ray source 2.

Further, it is also possible to supply the X-ray source 2 with the temperature-controlled gas G at least part of the period when the x-ray XL is not emitted from the X-ray source 2.

Further, in the first embodiment, it is configured to change the irradiation area of the measuring object S with the X-ray XL to obtain a plurality of images of the measuring object S, and acquire a three-dimensional data of the internal structure of the measuring object S based on the plurality of images. However, it is also possible to acquire the information about the internal structure of the measuring object S based on one image. That is, it is also possible to acquire a two-dimensional data of the internal structure of the measuring object S without irradiating the measuring object S with the X-ray XL from different angles.

Further, while the supply port 7 is arranged above (on the +Y side of) the X-ray source 2 in the first embodiment, it can alternatively be arranged on the +X or −X side of the X-ray source 2, or on the −Y side of the X-ray source 2. Further, the supply port 7 can include a plurality of supply ports 7 arranged to face the X-ray source 2. For example, the plurality of supply ports 7 can be arranged to encircle the housing 42.

Further, in the first embodiment, the supply port 7 can include a plurality of supply ports 7 arranged in the Z-axis direction.

<Second Embodiment>

Next, a second embodiment will be explained. In the following explanations, the same reference numerals will be assigned to the constitutive parts or components which are the same as or equivalent to those of the first embodiment described above, and the explanations of which will be simplified or omitted.

Figure 6:
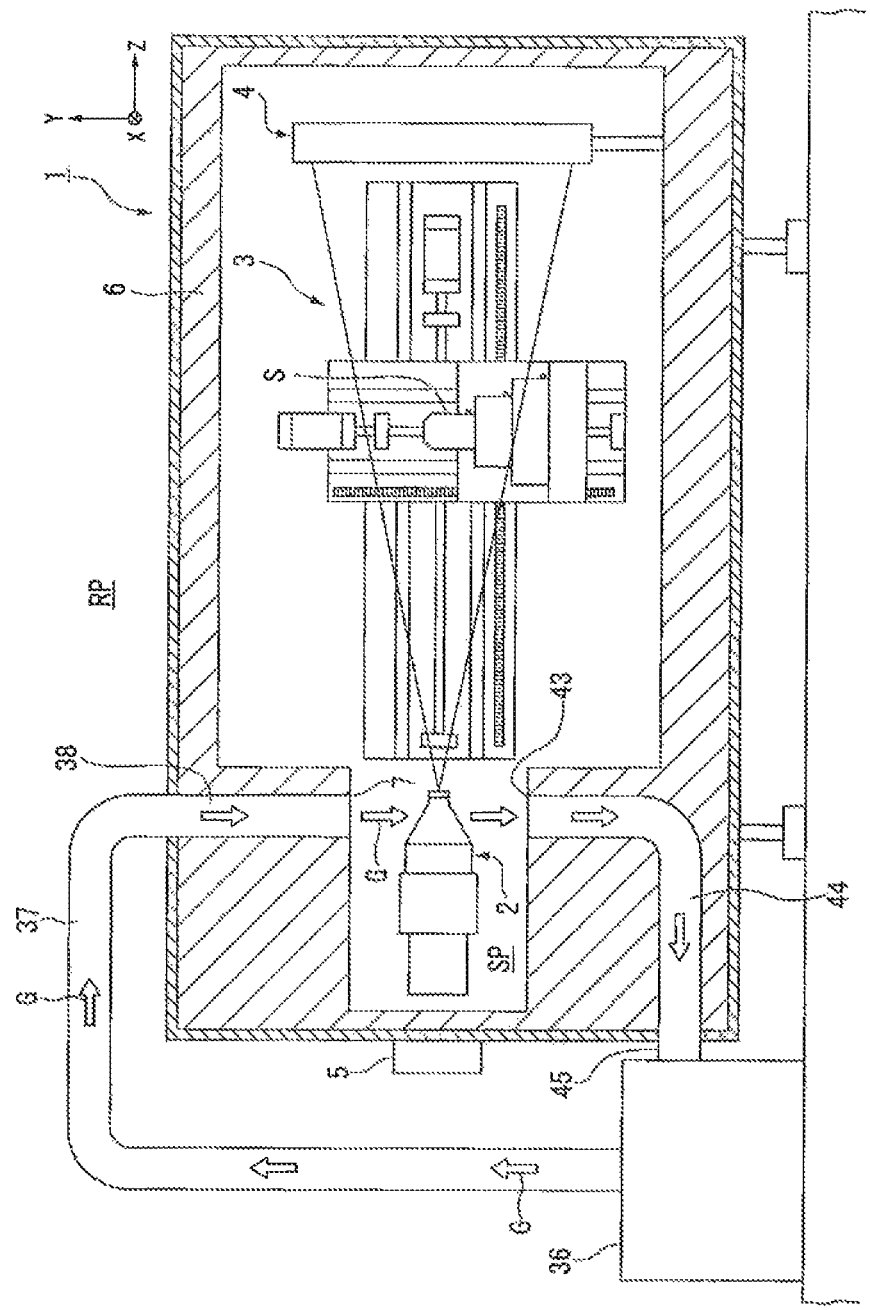
FIG. 6 is a view showing an example of a detection apparatus in accordance with, a second embodiment.

FIG. 6 is a view showing an example of a detection apparatus 1 in accordance with the second embodiment. In FIG. 6, the detection apparatus 1 includes the supply port 7 supplying the temperature-controlled gas G to at least part of the X-ray source 2, and a discharge port 43 discharging at least part of the gas in the internal space SP from the internal space SP. In the second embodiment, the gas discharged from the discharge port 43 includes at least part of the gas G supplied from the supply port 7.

The chamber member 6 has a duct 44. The duct 44 is formed to link the internal space SP and the external space RP. The opening at one end of the duct 44 is arranged to front on the internal space SP. The opening at the other end of the duct 44 is arranged to front on the external space RP. In the second embodiment, the opening at the one end of the duct 44 functions as the discharge port 43. At least part of the gas an the internal space SP is discharged from the discharge port 43 and, after flowing through the duct 44, let out to the external space RP via the opening at the other end of the duct 44.

In the second embodiment, the opening at the other end of the duct 44 is connected with one end of a duct 45. The other end of the duct 45 is connected to the adjusting device 36. In the second embodiment, the gas discharged from the discharge port 43 is sent to the adjusting device 36 through the flow passage of the duct 44 and duct 45 of the chamber member 6.

In the second embodiment, the adjusting device 36 controls the temperature of the gas discharged from the discharge port 43. The adjusting device 36 controls the temperature of the gas from the discharge port 43 and then sends the same to the supply port 7. The supply port 7 supplies at least part of the X-ray source 2 with the temperature-controlled gas G from the adjusting device 36.

In this manner, in the second embodiment a circulation system circulating the gas is established by the flow passage of the adjusting device 36 and duct 37, and the flow passage of the duct 38, internal space SP, duct 44, and duct 45.

In the second embodiment, the discharge port 43 is arranged to face at least part of the X-ray source 2. In the second embodiment, the supply port 7 is arranged above (on the +Y side of) the X-ray source 2 while the discharge port 43 is arranged below (on the −Y side of) the X-ray source 2. The X-ray source 2 is arranged between the supply port 7 and the discharge port 43.

In the second embodiment, the adjusting device 36 includes a vacuum system capable of sucking gas. With the vacuum system of the adjusting device 36 in operation, the discharge port 43 sucks at least part of the gas in the internal space SP. That is, in the second embodiment, the adjusting device 36 including the vacuum system 36 forcibly discharges at least part of the gas in the internal space SP from the internal space SP via the discharge port 43.

In the second embodiment, along with at least part of the supply of the gas G from the supply port 7, the adjusting device 36 discharges the gas from the discharge port 43. By virtue of this, in the internal space SP, a gas flow is generated from the supply port 7 toward the discharge port 43. The gas flow is formed up in the internal space SP by discharging the gas from the discharge port 43 along with at least part of the supply of the gas G from the supply port 7.

Further, the gas can also be discharged (sucked) from the discharge port 43 when the supply of the gas G from the supply port 7 is stopped. Further, the gas G can also be supplied from the supply port 7 when the discharge (suction) of the as from the discharge port 43 is stopped. For example, it is possible to alternatively carry out a first operation to supply the gas G from the supply port 7 without sucking the gas from the discharge port 43, and a second operation to suck the gas from the discharge port 43 while the supply of the gas G from the supply port 7 is stopped.

As explained above, in the second embodiment, it is also possible to restrain temperature change in the members including the X-ray source 2 contained in the internal space SP, and temperature change in the internal space SP per se.

Further, in the second embodiment, the adjusting device 36 includes a vacuum system allowing the discharge port) 43 to suck (forcibly discharge) the gas in the internal space SP. However, it is also possible that the adjusting device 36 does not include a vacuum system. For example, the gas in the internal space SP can be discharged naturally from the discharge port 43.

Further, in the second embodiment it is possible that the adjusting device 36 controls the temperature of the total gas from the discharge port 43 and sends the same to the supply port 7. Further, in the second embodiment, it is also possible that the adjusting device 36 controls the temperature of part of the gas from the discharge port 43 to send the same to the supply port 7, and releases the rest of the gas to the external space RP. Further, it is also possible that the adjusting device 36 releases the total gas from the discharge port 43 to the external space RP. In this case, the adjusting device 36 can take in some gas in the external space RP, for example, control the temperature of this gas, and send at least part of the temperature-controlled gas G to the supply port 7.

Further, in the second embodiment, although the gas discharged from the discharge port 43 is sent to the adjusting device 36, it can alternatively be released to the external space RP but not sent to the adjusting device 36

Further, in the above first and second embodiments, although the adjusting device 36 is arranged in the external space RP, it is also possible that the whole or part of the adjusting device 36 is arranged in the internal space SP. For example, the adjusting device 36 can take in some gas in the internal space SP, control the temperature of this gas, and send the temperature-controlled gas G to the supply port 7.

Further, while the supply port 7 is arranged above on the +Y side of) the X-ray source 2 in the second embodiment, it can alternatively be arranged on the +X or −X side of the X-ray source 2, or on the side of the X-ray source 2. Further, while the discharge port 43 is arranged below (on the −Y side of) the X-ray source 2 in the second embodiment, it can alternatively be arranged on the +X or −X side of the X-ray source 2, or on the +Y side of the X-ray source 2. Further, although the X-ray source 2 is arranged between the supply port 7 and the discharge port 43 in the second embodiment, the discharge port(s) 43 can be arranged on one or both of the +X side and the −X side of the X-ray source 2, for example, while the supply port 7 is still arranged on the +Y side of the X-ray source 2. Further, the supply port 7 can include a plurality of supply ports 7 arranged to face the X-ray source 2. Further, the discharge port 43 can also include a plurality of discharge ports 43 arranged to face the X-ray source 2. For example, the plurality of supply ports 7 and/or the plurality of discharge ports 43 can be arranged to encircle the housing 42.

Further, in the second embodiment, the supply port can include a plurality of supply ports 7 arranged in the Z-axis direction, and the discharge port 43 can also include a plurality of discharge ports 43 arranged in the Z-axis direction.

<Third Embodiment>

Next, a third embodiment will be explained, in the following explanations, the same reference numerals will be assigned to the constitutive parts or components which are the same as or equivalent to those of the embodiments described above, and the explanations of which will be simplified or omitted.

Figure 7:
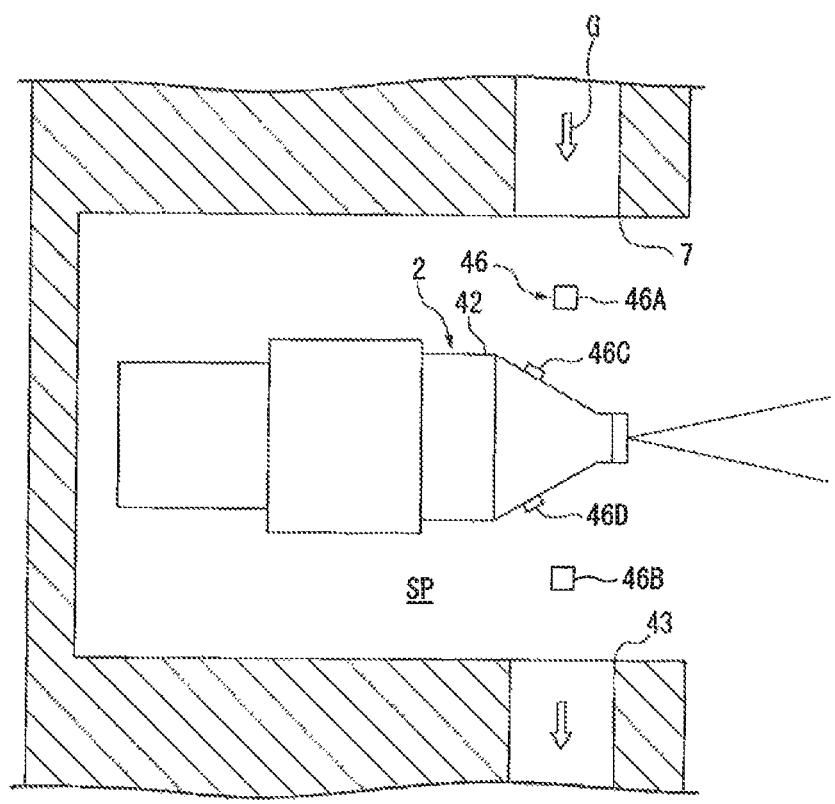
FIG. 7 is a view showing an example of a detection apparatus in accordance with a third embodiment.

FIG. 7 is a view showing part of a detection apparatus 1 in accordance with the third embodiment. Further, in the following explanations, while it is exemplified that the supply port 7 is arranged on the +Y side of the X-ray source 2 and the discharge port 43 is an or the −Y side, as described above, however, it is possible to arbitrarily determine the number and position of the supply ports 7 and discharge ports 43. Further, it is also possible to leave out the discharge port 43.

In FIG. 7, the detection apparatus 1 includes a temperature sensor 46 detecting the temperature of at least one of the X-ray source 2 and the internal space SP. In the third embodiment, the temperature sensor 46 includes temperature sensors 46A, 46E, 46C, and 46D. The temperature sensor 46A is arranged between the supply port 7 and the X-ray source 2. The temperature sensor 46A is situated away from both the supply port 7 and the X-ray source 2. The temperature sensor 46B is arranged between the discharge port 43 and the X-ray source 2. The temperature sensor 46B is situated away from both the discharge port 43 and the X-ray source 2. The temperature sensor 46C is connected on the external surface of the housing 42 of the X-ray source 2. The temperature sensor 46C is arranged to face the supply port 7. The temperature sensor 46D is also connected on the external surface of the housing 42 of the X-ray source 2. The temperature sensor 46D is arranged to face the discharge port 43.

The temperature sensors 46A and 46B can detect the temperature in the internal space SP. The temperature sensor 46A can detect the temperature of the space between the supply port 7 and the X-ray source 2. The temperature sensor 46B can detect the temperature of the space between the discharge port 43 and the X-ray source 2. The temperature sensors 46C and 46D can detect the temperature of the X-ray source 2.

In the third embodiment the temperature sensors 46A to 46D detect the temperatures in the calibration (step SA1 of FIG. 3). Further, in the third embodiment, the temperature sensors 46A to 46D detect the temperatures in irradiating the measuring object S with the X-ray XL and detecting the transmission X-ray transmitted through the measuring object S (step SA2 of FIG. 3) in other words, the temperature sensors 46A to 46D detect the temperature of at least one of the X-ray source 2 and the internal space SP at least when the X-ray source 2 is emitting the X-ray XL.

The detection results of the temperature sensors 46A to 46D are outputted to the control device 5. In the third embodiment, the control device 5 controls the adjusting device 36 based on the detection results of the temperature sensors 46A to 46D. The adjusting device 36 controls the temperature of the gas G supplied from the adjusting device 36 based on the detection results of the temperature sensors 46A to 46D. The control device 5 controls the adjusting device 36 to control the temperature of the gas G sent out from the adjusting device 36 based on the detection results of the temperature sensors 46A to 46D such that the temperature of at least one of the X-ray source 2 and the internal space SP substantially reaches a target temperature. In other words, the control device 5 controls the adjusting device 36 to control the temperature of the gas G sent out from the adjusting device 36 based on the detection results of the temperature sensors 46A to 46D to substantially reduce the difference between the detection values of the temperature sensors 46A to 46D, and the target value of the temperature of at least one of the X-ray source 2 and the internal space SP.

As explained above, in the third embodiment, it is also possible to restrain temperature change in the members including the X-ray source 2 contained in the internal, space SP, and temperature change in the internal space SP per se.

<Fourth Embodiment>

Next, a fourth embodiment will be explained. In the following explanations, the same reference numerals will be assigned to the constitutive parts or components which are the same as or equivalent to those of the embodiments described above, and the explanations of which will be simplified or omitted.

Figure 8:
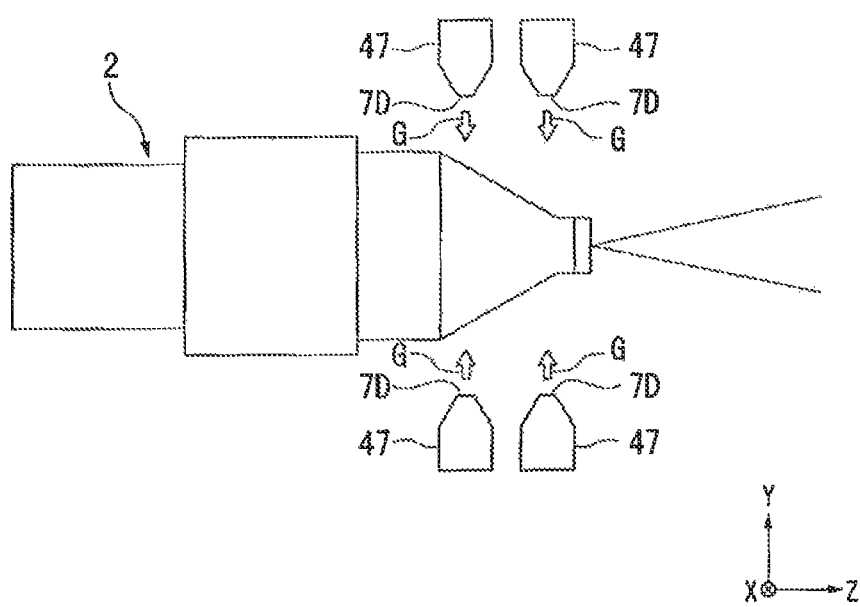
FIG. 8 is a view showing an example of a detection apparatus in accordance with a fourth embodiment.

FIG. 8 is a view showing part of a detection apparatus 1 in accordance with the fourth embodiment. In the fourth embodiment, the detection apparatus 1 is arranged in the internal space SP, and includes a plurality of nozzle members 47 with supply ports 7D. In the fourth embodiment, the detection apparatus 1 has four nozzle members 47. Each of the nozzle members 47 has a supply port 7D.

The supply ports 7D of the nozzle mashers 47 supply the temperature-controlled gas G to at least part of the X-ray source 2. The nozzle members 47 are arranged on at least part of the periphery of the X-ray source 2. The nozzle members 47 are arranged such that the supply ports 7D face the external surface of the housing 42.

In the fourth embodiment, the nozzle members 47 are movable with respect to the X-ray source 2. The detection apparatus 1 has a drive system capable of moving the nozzle members 47. The control device 5 can control the drive system to move the nozzle members 47 with respect to the X-ray source 2. The control device 5 can move the nozzle members 47 to supply the gas G from the supply ports 7D in any area on the external surface of the housing 42.

As explained above, in the fourth embodiment, it is also possible to restrain temperature change in the members including the X-ray source 2 contained in the internal space SP, and temperature change in the internal, space SP per se.

Further, in the fourth embodiment, an arbitrary number of the nozzle members 47 (the supply ports 7D) can be arranged; the number of the nozzle members 47 (the supply ports 7D) can also be one two, three, or more than four.

Further, in the fourth embodiment, it is also possible to provide a temperature sensor detecting the temperature of at least one of the X-ray source 2 and the internal space SP for controlling the temperature of the gas G supplied from the supply ports 7D based on the detection result of the temperature sensor.

<Fifth Embodiment>

Next, a fifth embodiment will be explained. In the following explanations, the same reference numerals will be assigned to the constitutive parts or components which are the same as or equivalent to those of the embodiments described above, and the explanations of which will be simplified or omitted.

Figure 9:
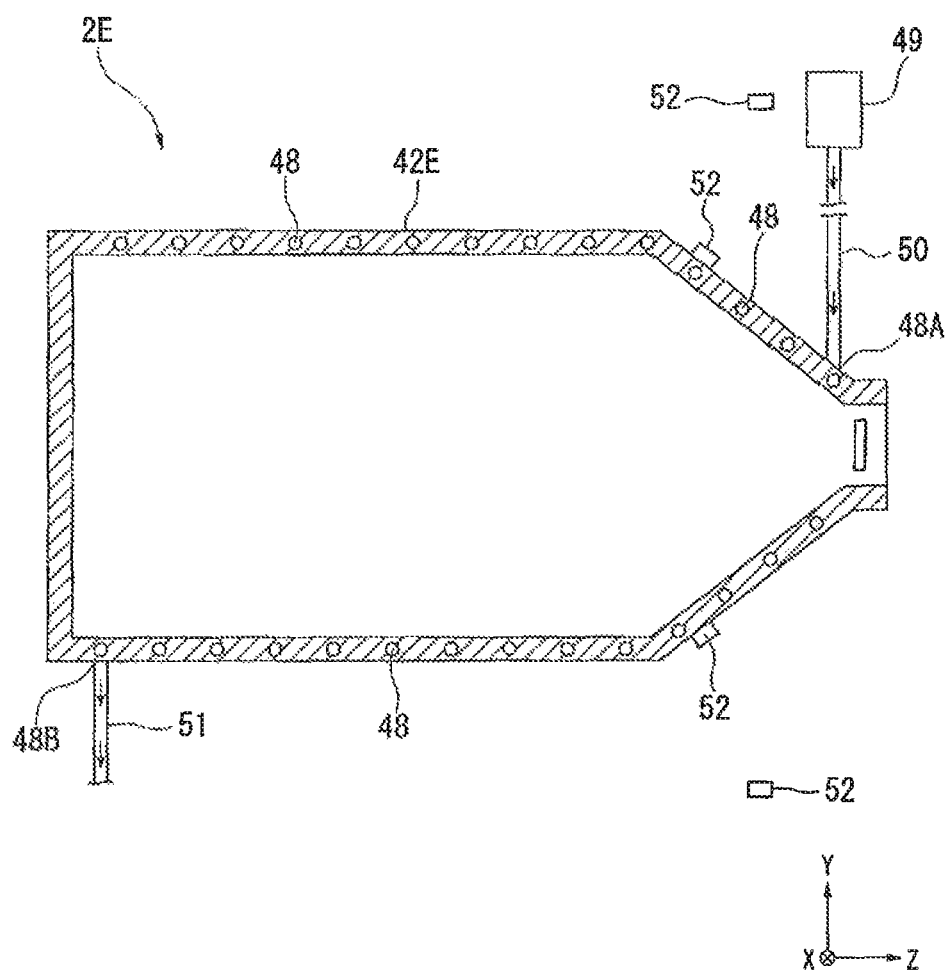
FIG. 9 is a view showing an example of a detection apparatus in accordance with a fifth embodiment.

FIG. 9 is a view showing part of an X-ray source 2E in accordance with the fifth embodiment. In the fifth embodiment, the X-ray source 22 has a housing 42E. The housing 42E has a duct 48.

In the fifth embodiment, the detection apparatus 1 has an adjusting device 49 supplying a temperature-controlled fluid to the duct 48 of the housing 42E. The adjusting device 49 can supply, for example, a temperature-controlled liquid, or a temperature-controlled gas or aerosol.

The duct 48 is formed into a spiral shape. The duct 48 has an inlet 48A and an outlet 48B. The adjusting device 49 is connected with the inlet 48A through a duct 50. The fluid is sent out from the adjusting device 49 to the inlet 48A through the flow passage of the duct 50. The fluid sent from the adjusting device 49 to the inlet 48A flows through the duct 48. The fluid flowing through the duct 48 flows out from the outlet 48B.

The outlet 48B is connected with a duct 51. The fluid out of the outlet 48B flows through the flow passage of the duct 51. The fluid out of the outlet 48B can be discharged to such as the external space RP. Further, the fluid out of the outlet 48B can be sent back to the adjusting device 49. Then, the adjusting device 49 can control the temperature of the fluid discharged from the outlet 48B. Then, the adjusting device 49 can send, again to the duct 48, the fluid discharged from the outlet 48B and temperature-controlled by the adjusting device 49.

Further, in the fifth embodiment, at least one temperature sensor 52 can be provided to detect the temperature of at least one of the X-ray source 2E and the internal space SP. The adjusting device 49 can control the temperature of the fluid supplied to the duct 48 based on the detection result (s) of the temperature sensor(s) 52.

As explained above, in the fifth embodiment, it is also possible to restrain temperature change in the members including the X-ray source 2E contained in the internal space SP, and temperature change in the internal space SP per se.

<Sixth Embodiment>

Next, a sixth embodiment will be explained. In the following explanations, the same reference numerals will be assigned to the constitutive parts or components which are the same as or equivalent to those of the embodiments described above, and the explanations of which will be simplified or omitted.

FIG. 10 is a view showing an example of a detection apparatus 1 in accordance with the sixth embodiment. In FIG. 10, the detection apparatus 1 includes a duct 38F which is connected with a supply port 7F and through which a gas Gf flows to be supplied to the supply port 7F, and a temperature adjustment member 53 (an example of a temperature-controlled member) arranged in the duct 38F to be temperature-controlled. The duct 38F is formed, for example, in the chamber member 6. The supply port 7F includes the opening of one end of the duct 38F.

In the sixth embodiment, the gas Gf through contact with the temperature adjustment member 53 is supplied from the supply port 7F. By virtue of this, the Gf temperature-controlled by the temperature adjustment member 53 is supplied from the supply port 7F to at least part of the X-ray source 2.

The temperature adjustment member 53 includes such as a Peltier element. The Peltier element is controlled by the control device 5. The control device 5 controls the temperature adjustment member 53 including the Peltier element to supply the gas Gf at a target temperature from the supply port 7F.

As explained above, in the sixth embodiment, it is also possible to restrain temperature change in the members including the X-ray source 2 contained in the internal space SP, and temperature change in the internal space SP per se.

Further, in the sixth embodiment, it is also possible to provide a temperature sensor detecting the temperature of at least one of the X-ray source 2 and the internal space SP for controlling the temperature adjustment member 53 based on the detection result of the temperature sensor.

Further, it is also possible to arrange the temperature adjustment member 53 in a flow passage formed in a different member from the chamber member 6. For example, the temperature adjustment member 53 can be arranged in the flow passage of a nozzle member arranged in the internal space SP. It is possible to restrain temperature change in the X-ray source 2 and the like by supplying the gas through contact with the temperature adjustment member 53 to the X-ray source 2 from a supply port of the nozzle member.

<Seventh Embodiment>

Next, a seventh embodiment will be explained. In the following explanations, the same reference numerals will be assigned to the constitutive parts or components which are the same as or equivalent me those of the embodiments described above, and the explanations of which will be simplified or omitted.

FIG. 11 is a view showing an example of a detection apparatus 1 in accordance with the seventh embodiment. In FIG. 11, the detection apparatus 1 includes a duct 38G which is connected with a supply port 7G and through which a gas Gg flows to be supplied to the supply port 7G, and a temperature adjustment member 54 arranged in the duct 38G to be temperature-controlled. The duct 38G is formed, for example, in the chamber member 6. The supply port 7G includes the opening of one end of the duct 38G.

In the seventh embodiment, the gas Gg through contact with the temperature adjustment member 54 is supplied from the supply port 7G. By virtue of this, the gas Gg temperature-controlled by the temperature adjustment member 54 is supplied from the supply port 7G to at least part of the X-ray source 2.

In the seventh embodiment, the detection apparatus 1 has a supply device 55 supplying a temperature-controlled liquid to the temperature adjustment member 54. The supply device 55 operates on such as electric power. In the seventh embodiment, the temperature adjustment member 54 has a duct. The duct has an inlet 54A to which the liquid flows in, and an outlet 54B from which the liquid flows out. The temperature adjustment member 54 is made from such as a metal.

The supply device 55 is connected with, the inlet 54A through another duct. The supply device 55 sends the temperature-controlled liquid to the inlet 54A through the flow passage of this duct. The liquid sent out from the supply device 55 and let into the inlet 54A flows through the duct of the temperature adjustment member 54. By virtue of this, the temperature adjustment member 54 is temperature-controlled with the liquid from the supply device 55.

In the seventh embodiment, the supply device 55 is controlled by the control device 5. The control device 5 controls the supply device 55 to supply the gas Gg at a target temperature from the supply port 7G.

In the seventh embodiment, the outlet 54B is connected with a recovery device 56 through still another duct. The liquid flowing through the duct of the temperature adjustment member 54 and out of the outlet 54B is recovered by the recovery device 56 through the flow passage of this duct.

In the seventh embodiment, the recovery device 56 can send the recovered liquid to the supply device 55. The supply device 55 can also control the temperature of the liquid from the recovery device 56. Further, the supply device 55 can control the temperature of the liquid from the recovery device 56, and then supply the temperature-controlled liquid to the temperature adjustment member 54.

In the seventh embodiment, the supply device 55 and the recovery device 56 are arranged outside of the duct 38G. Further, at least part of the supply device 55 can be arranged in the duct 38G. Further, at least part of the recovery device 56 can be arranged in the duct 38G.

As explained above, in the seventh embodiment, it is also possible to restrain temperature change in the members including the X-ray source 2 contained in the internal space SP, and temperature change in the internal space SP per se.

Further, in the seventh embodiment, it is also possible to provide a temperature sensor detecting the temperature of at least one of the X-ray source 2 and the internal space SP for controlling the supply device 55 based on the detection result of the temperature sensor.

Further, it is also possible to arrange the temperature adjustment member 54 in a flow passage formed in a different member from the chamber member 6. For example, the temperature adjustment member 54 can be arranged in the flow passage of a nozzle member arranged in the internal space SP. It is possible to restrain temperature change in the X-ray source 2 and the like by supplying the gas through contact with the temperature adjustment member 54 to the X-ray source 2 from a supply port of the nozzle member.

Further, in the seventh embodiment, although a liquid is supplied to the temperature adjustment member 54, a temperature-controlled as can be supplied instead.

<Eighth Embodiment>

Next, an eighth embodiment will be explained. In the following explanations, the same reference numerals will be assigned to the constitutive parts or components which are the same as or equivalent to those of the embodiments described above, and the explanations of which will be simplified or omitted.

Figure 12:
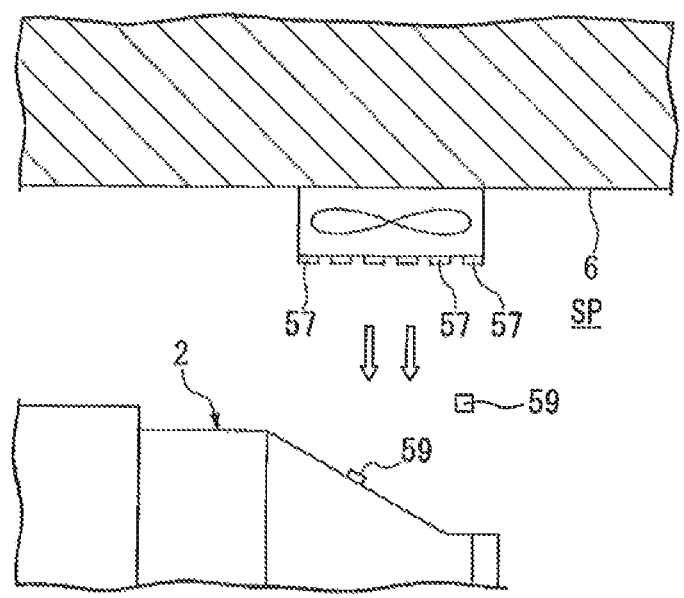
FIG. 12 is a view showing an example of a detection apparatus in accordance with an eighth embodiment.

FIG. 12 is a view showing an example of a detection apparatus 1 in accordance with the eighth embodiment. In FIG. 12, the detection apparatus 1 includes a temperature adjustment member 57 arranged in the internal space SP to be temperature-controlled. Further, in the eighth embodiment, the detection apparatus 1 includes a generator device 58 arranged in the internal space SP and capable of generating a gas flow. The generator device 58 includes such as a blower.

In the eighth embodiment, the temperature adjustment member 57 is arranged between the generator device 58 and the X-ray source 2. The generator device 58 generates the gas flow from the temperature adjustment member 57 toward the X-ray source 2. By virtue of this, the gas temperature-controlled through contact with the temperature adjustment member 57 is supplied to at least part of the X-ray source 2.

In the eighth embodiment, the temperature adjustment member 57 includes a plurality of temperature adjustment members 57 arranged at intervals. The gas from the generator device 58 flows through the interspaces between the plurality of temperature adjustment members 57 to be supplied to the X-ray source 2.

Each of the temperature adjustment members 57 includes such as a Peltier element. The Peltier elements are controlled by the control device 5. The control device 5 controls the temperature adjustment members 57 including the Peltier elements such that the gas for supply to the X-ray source 2 can reach a target temperature.

In the eighth embodiment, the detection apparatus 1 includes at least one temperature sensor 59 detecting the temperature of at least one of the X-ray source 2 and the internal space SP. The control device 5 can also control the temperature adjustment members 57 based on the detection result of the temperature sensor(s) 59.

As explained above, in the eighth embodiment, it is also possible to restrain temperature change in the members including the X-ray source 2 contained in the internal space SP, and temperature change in the internal space SP per se.

<Ninth Embodiment>

Next, a ninth embodiment will be explained. In the following explanations, the same reference numerals will be assigned to the constitutive parts or components which are the same as or equivalent to those of the embodiments described above, and the explanations of which will be simplified or omitted.

FIG. 13 is a view showing an example of a detection apparatus 1 in accordance with the ninth embodiment. In FIG. 13, the detection apparatus 1 includes a temperature adjustment member 60 arranged in the internal space SP to be temperature-controlled. Further, in the ninth embodiment, the detection apparatus 1 includes a generator device 61 arranged in the internal space SP and capable of generating a gas flow. The generator device 61 includes such as a blower.

In the ninth embodiment, the temperature adjustment member 60 is arranged between the generator device 61 and the X-ray source 2. The generator device 61 generates the gas flow from the temperature adjustment member 60 toward the X-ray source 2. By virtue of this, the gas temperature-controlled through contact with the temperature adjustment member 60 is supplied to at least part of the X-ray source 2.

In the ninth embodiment, the detection apparatus 1 has a supply device 62 supplying a temperature-controlled liquid to the temperature adjustment member 60. The supply device 62 operates on such as electric power. In the ninth embodiment, the temperature adjustment member 60 has a duct. The duct has an inlet 60A to which the liquid flows in, and an outlet 60B from which the liquid flows out. The temperature adjustment member 60 is made from such as a metal.

The supply device 62 is connected with the inlet 60A through another duct. The supply device 62 sends the temperature-controlled liquid to the inlet 60A through the flow passage of this duct. The liquid sent out from the supply device 62 and let into the inlet 60A flows through the duct of the temperature adjustment member 60. By virtue of this, the temperature adjustment member 60 is temperature-controlled with the liquid from the supply device 62.

In the ninth embodiment, the temperature adjustment member 60 has a passage 60R, through which gas can flow. The gas from the generator device 61 flows through the passage 60R and is supplied to the X-ray source 2.

In the ninth embodiment, the supply device 62 is controlled by the control device 5. The control device 5 controls the supply device 62 such that the gas for supply to the X-ray source 2 reaches a target temperature.

In the ninth embodiment, the outlet 60B is connected with a recovery device 63 through still another duct. The liquid flowing through the duct of the temperature adjustment member 60 and out of the outlet 60B is recovered by the recovery device 63 through the flow passage of this duct.

In the ninth embodiment, the recovery device 63 can send the recovered liquid to the supply device 62. The supply device 62 can also control the temperature of the liquid from the recovery device 63. Further, the supply device 62 can control the temperature of the liquid from the recovery device 63, and then supply the temperature-controlled liquid to the temperature adjustment member 60.

In the ninth embodiment, the supply device 62 and the recovery device 63 can be arranged outside of the internal space SP. Alternatively, at least part of the supply device 62 can be arranged in the external space RP, and/or at least part of the recovery device 63 can be arranged in the external space RP.

In the ninth embodiment, the detection apparatus 1 includes at least one temperature sensor 64 detecting the temperature of at least one of the X-ray source 2 and the internal space SP. The control device 5 can also control the supply device 62 based on the detection result of the temperature sensor (s) 64. That is, the supply device 62 can also control the temperature of the liquid for supply to the temperature adjustment member 60 based on the detection result of the temperature sensor (s) 64.

As explained above, in the ninth embodiment, it is also possible to restrain temperature change in the members including the X-ray source 2 contained in the internal space SP, and temperature change in the internal space SP per se.

Further, in the ninth embodiment, although a liquid is supplied to the temperature adjustment member 60, a temperature-controlled gas can be supplied instead.

<Tenth Embodiment>

Next, a tenth embodiment will be explained. In the following explanations, the same reference numerals will be assigned to the constitutive parts or components which are the same as or equivalent to those of the embodiments described above, and the explanations of which will be simplified or omitted.

FIG. 14 is a view showing an example of a detection apparatus 1 in accordance with the tenth embodiment. In FIG. 14, the detection apparatus 1 includes an adjusting device 65 adjusting the temperature of at least part of the chamber member 6 defining the internal space SP.

In the tenth embodiment, the adjusting device 65 includes a plurality of Peltier elements 65P arranged on at least part of the chamber member 6. In the tenth embodiment, the Peltier elements 65P are arranged to face the X-ray source 2. In the tenth embodiment, the Peltier elements 65P are arranged on the internal surface of the chamber member 6 fronting on the internal space SF.

Further, at least some of the Peltier elements 65P can be arranged inside the chamber member 6. Further, at least some of the Peltier elements 65P can be arranged on the external surface of the chamber member 6.

The adjusting device 65 is controlled by the control device 5. The control device 5 controls the adjusting device 65 including the Peltier elements 65P such that at least one of the X-ray source 2, the chamber member 6, and the internal space SP can reach a target temperature.

As explained above, in the tenth embodiment, it is also possible to restrain temperature change in the members including the X-ray source 2 contained in the internal space SP, and temperature change in the internal space SP per se.

Further, in the tenth embodiment, it is also possible to provide a temperature sensor detecting the temperature of at least one of the X-ray source 2 and the internal space SP for controlling the adjusting device 65 based on the detection result of the temperature sensor.

Further, while the adjusting device 65 is provided on the chamber member 6 having the supply port 7 in the tenth embodiment, it can also be provided on the chamber member 6 without a supply port such as that explained in reference to FIGS. 12 and 13.

<Eleventh Embodiment>

Next, an eleventh embodiment will be explained. In the following explanations, the same reference numerals will be assigned to the constitutive parts or components which are the same as or equivalent to those of the embodiments described above, and the explanations of which will be simplified or omitted.

FIG. 15 is a view showing an example of a detection apparatus 1 in accordance with the eleventh embodiment. In FIG. 15, the detection apparatus 1 includes an adjusting device 66 adjusting the temperature of at least part of a chamber member 6K defining the internal space SP.

In the eleventh embodiment, the chamber member 6K has a duct 67. In the eleventh embodiment, the duct 67 is arranged on at least part of the periphery of the X-ray source 2. The adjusting device 66 supplies a temperature-controlled fluid to the duct 67 of the chamber member 6K.

In the eleventh embodiment, the adjusting device 66 has a supply device 68 supplying a temperature-controlled liquid to the duct 67. The supply device 68 operates on such as electric power. The duct 67 has an inlet 67A to which the liquid flows in, and an outlet 67B from which the liquid flows out.

The supply device 68 is connected with the inlet 67A through another duct. The supply device 68 sends the temperature-controlled liquid to the inlet 67A through the flow passage of this duct. The liquid sent out from the supply device 68 and let into the inlet 67A flows through the duct 67. By virtue of this, the chamber member 6K is temperature-controlled with the liquid from the supply device 68.

In the eleventh embodiment, the supply device 68 is controlled by the control device 5. The Control device 5 controls the supply device 68 such that at least one of the X-ray source 2, the chamber member 6, and the internal space SP can reach a target temperature.

In the eleventh embodiment, the outlet 67B is connected with a recovery device 69 through still another duct. The liquid flowing through the duct 67 and out of the outlet 67B is recovered by the recovery device 69 through the flow passage of this duct.

In the eleventh embodiment, the recovery device 69 can send the recovered liquid to the supply device 68. The supply device 68 can also control the temperature of the liquid from the recovery device 69. Further, the supply device 68 can control the temperature of the liquid item the recovery device 69, and then supply the temperature-controlled liquid to the duct 67.

In the eleventh embodiment, the supply device 68 and the recovery device 69 are arranged outside of the internal space SP. Further, at least part of the supply device 68 can be arranged in the internal space SP. Further, at least part of the recovery device 69 can be arranged in the internal space SP.

As explained above, in the eleventh embodiment, it is also possible to restrain temperature change in the members including the X-ray source 2 contained in the internal space SP, and temperature chance in the internal space SP per se.

Further, in the eleventh embodiment, it is also possible to provide a temperature sensor detecting the temperature of at least one of the X-ray source 2 and the internal space SP for controlling the supply device 68 based on the detection result of the temperature sensor.

Further, in the eleventh embodiment, although a liquid is supplied to the duct 67, a temperature-controlled gas or aerosol can be supplied instead.

Further, while the adjusting device 66 is provided in the chamber member 6 having the supply port 7 in the eleventh embodiment, it can also be provided in the chamber member 6 without a supply port such as that explained in reference to FIGS. 12 and 13.

<Twelfth Embodiment>

Next, a twelfth embodiment will be explained, the following explanations, the same reference numerals will be assigned to the constitutive parts or components which are the same as or equivalent to those of the embodiments described above, and the explanations of which will be simplified or omitted.

Figure 16:
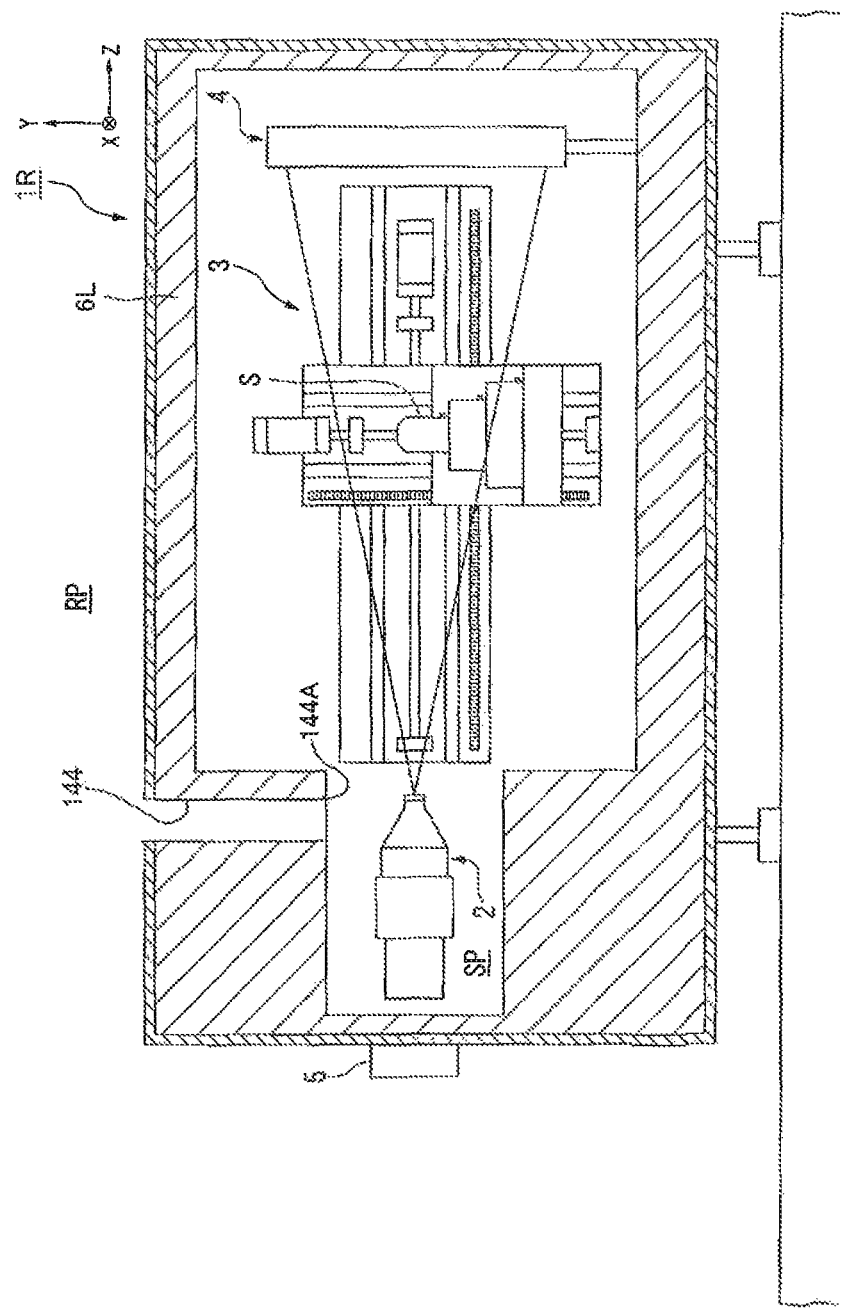
FIG. 16 is a view showing an example of a detection apparatus in accordance with a twelfth embodiment.

FIG. 16 is a view showing an example of a detection apparatus 1 in accordance with the twelfth embodiment. A chamber member 6L of the detection apparatus 1 in accordance with the twelfth embodiment is not provided with a supply port supplying a temperature-controlled gas or the like but, as will be described hereinafter, is provided with a discharge port discharging the gas in a first space SP1. As shown in FIG. 16, a partitionment portion 100 divides the internal space SP into the first space SP1 and a second space SP2. Then, the chamber member 6L is provided, with a duct 144 defining a as flow passage communicating the first space SP with the external space RP. A discharge port 144A, which is an opening of the duct 144 or the first space SP side, is arranged above the X-ray source 2 (in the +Y direction). The duct 144 is formed to extend upward from the discharge port 144A (in the +Y direction).

When the as around the X-ray source 2 is warmed by the heat produced due to driving the X-ray source 2 then the gas around the X-ray source 2 decreases in specific gravity and thus flows upward. Here, because the discharge port 144A is arranged above the X-ray source 2 while the duct 144 extends upward as described above, it is possible to efficiently discharge the warmed gas around the X-ray source 2 to the external space RP through the duct 144. At this time, since the cues around the X-ray source 2 undergoes an exchange, it is possible to restrain local temperature rise an the first space SP. That is, it is possible to restrain the temperature rise in the members of the detection apparatus 1R disposed in the first space SP, thereby making it possible to restrain the probability for these members to undergo thermal deformation. By virtue of this, it is possible to restrain decrease in the detection accuracy of the detection apparatus 1R.

Further, whereas it is not necessary to arrange the discharge port 144A above the X-ray source 2, it is possible to arrange the discharge port 144A, for example, below the X-ray source 2. In such case, it is still possible to discharge the gas around the X-ray source 2 to the external space RP through the discharge port 144A. Further, it is also possible to provide a generator device (such as a blower) for moving the gas around the X-ray source 2 toward the discharge port 144A. Further, whereas it is not necessary for the duct 144 to be linear, it is possible for the duct 144 to take any shape as appropriate. Further, whereas it is not necessary for the duct 144 (and the discharge port 144A) to be one, it is possible to form a plurality of ducts 144 and discharge ports 144A far the chamber member 6L.

<Thirteenth Embodiment>

Next, a thirteenth embodiment will be explained. In the following explanations, the same reference numerals will be assigned to the constitutive parts or components which are the same as or equivalent to those of the embodiments described above, and the explanations of which will be simplified or omitted.

Figure 17:
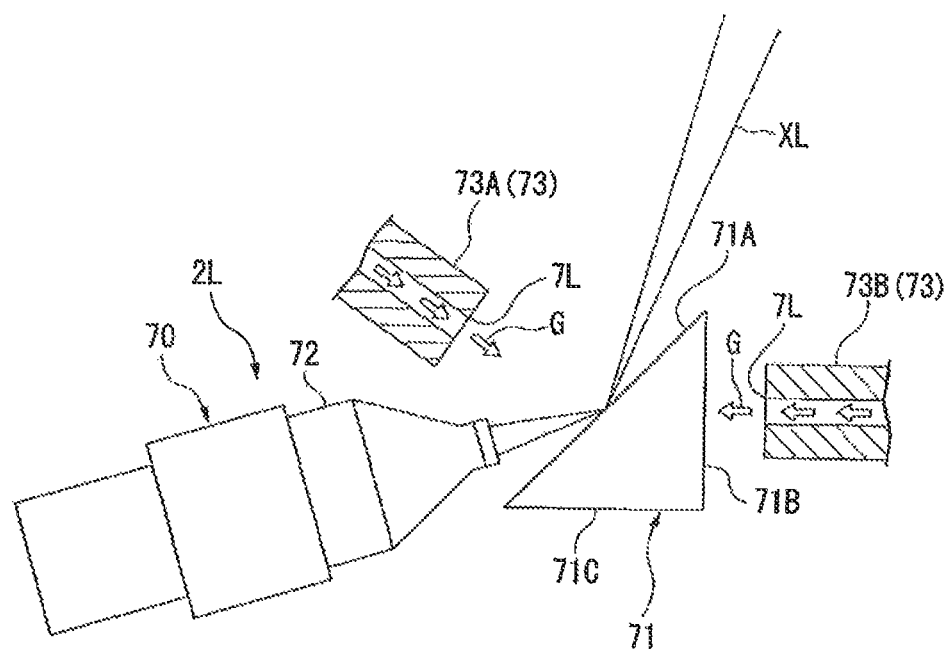
FIG. 17 is a view showing an example of a detection apparatus in accordance with a thirteenth embodiment.

FIG. 17 is a view showing part of an X-ray source 2L in accordance with the thirteenth embodiment. In the thirteenth embodiment, the X-ray source 2L is referred to as a so-called reflection type. In the thirteenth embodiment, the x-ray source 2L has an electron emission portion 70 including a filament and an electron conduction member, and a target 71. In the thirteenth embodiment, the electron mission portion 70 includes a housing 72 accommodating the filament and the electron conduction member. The target 71 is arranged outside of the housing 72 (the electron emission portion 70). The electron conduction member of the electron emission portion 70 conducts electrons generated from the filament to the target 71. The electrons from the electron emission portion 70 collide against the target 71. The target 71 generates the X-ray XL by the collision of the electrons.

In the thirteenth embodiment, the target 71 has a first surface 71A irradiated with the electrons from the electron emission portion 70, and a second surface 71B and a third surface 71C which face toward a different direction with the first surface 71A. In the thirteenth embodiment, the first surface 71A is irradiated with the electrons to generate the X-ray XL.

In the thirteenth embodiment, the detection apparatus 1 includes a nozzle member 73 having supply ports 7L supplying the temperature-controlled gas G to the target 71. In the thirteenth embodiment, the nozzle member 73 includes a first nozzle member 73A having one supply port 7L supplying the gas G to the first surface 71A, and a second nozzle member 73B having the other supply port 7L supplying the gas G to the second surface 71B. The supply port 7L of the first nozzle member 73A faces the first surface 71A. The supply port 7L of the second nozzle member 73B faces the second surface 71B.

Further, another supply port 7L can be arranged to supply the gas G to the third surface 71C. Further, the first surface 71A is supplied with the gas G while the second and third surfaces 71B and 71C can not be supplied with the gas G, or the second surface 71B is supplied with the gas G while the first and third surfaces 71A and 71C can not be supplied with the gas G, or the third surface 71C is supplied with the gas G while the first and second surfaces 71A and 71B can not be supplied with the gas G. Further, the second and third surfaces 71B and 71C are supplied with the gas G while the first surface 71A can not be supplied with the gas G, or the first and third surfaces 71A and 71C are supplied with the gas G while the second surface 71B can not be supplied with the gas G.

As explained above, the thirteenth embodiment, it is also possible to restrain temperature change in the members including the X-ray source 2L contained in the internal space SP, and temperature change in the internal space SP per se.

<Fourteenth Embodiment>

Next, a fourteenth embodiment will be explained. In, the following explanations, the same reference numerals will be assigned to the constitutive parts or components which are the same as or equivalent to those of the embodiments described above, and the explanations of which will be simplified or omitted.

Figure 18:
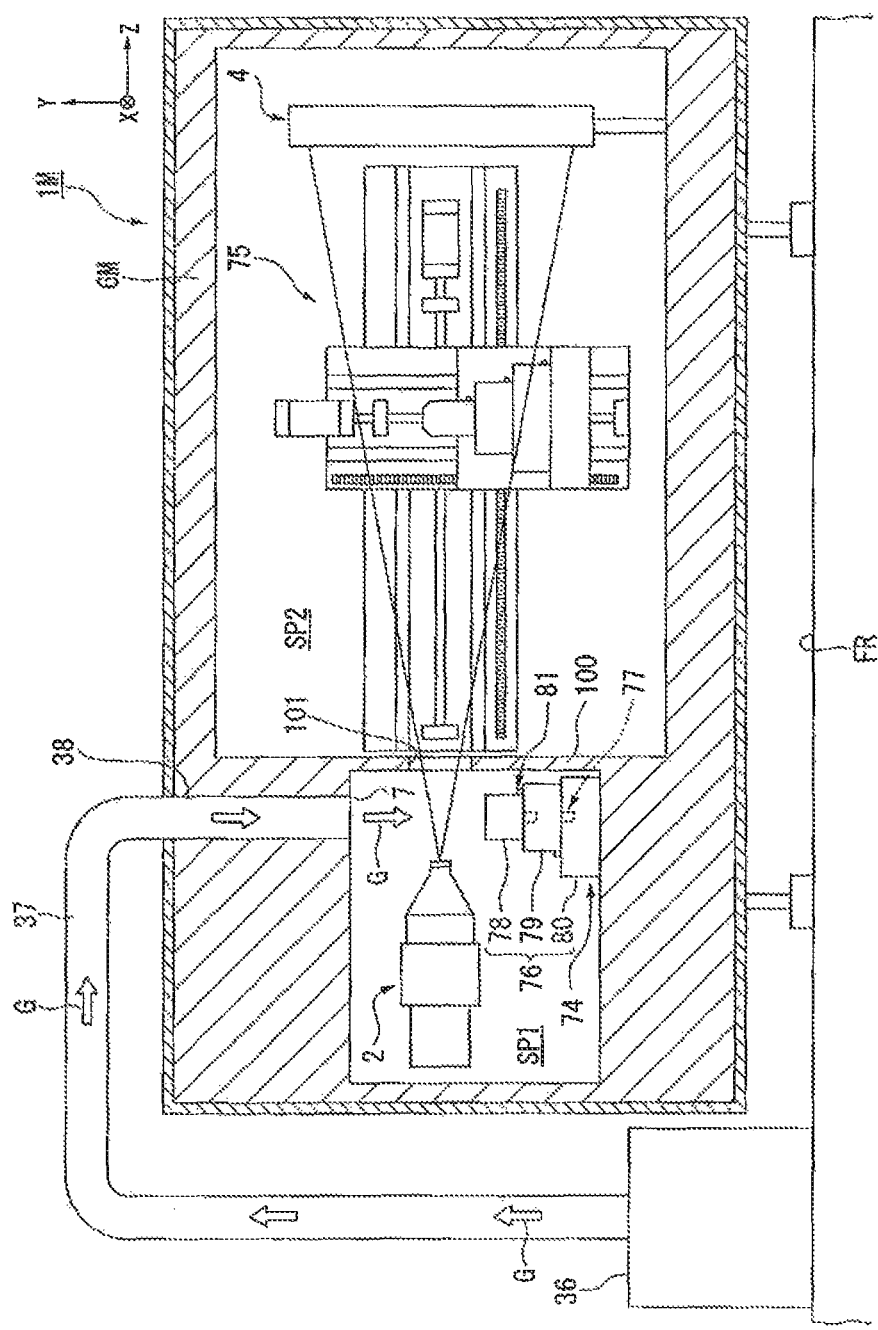
FIG. 18 is a view showing an example of a detection apparatus in accordance with a fourteenth embodiment.

FIG. 18 is a view showing part of the X-ray source 2F in accordance with the fourteenth embodiment. In the fourteenth embodiment, a detection apparatus 1M has a chamber member 6M defining an internal space.

In the fourteenth embodiment, the internal space defined by the chamber member 6M includes a first space SP1 in which the X-ray source 2 is arranged and the gas 2 is supplied from the supply port 7, and a second space SP2 in which the detector 4 is arranged. The first space SP1 and the second space SP2 are partitioned by a partitionment portion 100. The partition portion 100 has a passage portion 101 through which the X-ray XL from the X-ray source 2 is passable. The X-ray XL emitted from the X-ray source 2 is supplied to the second space SP2 through the passage portion 101.

The temperature of the X-ray source 2 arranged in the first space SP1 is controlled with the gas G supplied from the supply port 7 to the first space SP1.

In the fourteenth embodiment, the detection apparatus 1M includes a first stage device 74 arranged in the first space SP1, and a second stage device 75 arranged in the second space SP2. In the fourteenth embodiment, the second stage device 75 has the same configuration with the stage device 3 explained in the aforementioned embodiments. Further, the measuring system measuring the position of the stage of the second stage device 75 has the same configuration with the measuring system 28 explained in the aforementioned embodiments.

The first stage device 74 includes a stage 76, and a drive system 77 driving the stage 76. The stage 76 includes a table 78 capable of retaining a measuring object, a first movable member 79 movably supporting the table 78, and a second movable member 80 movably supporting the first movable member 79. The first movable member 79 is movable in such as the X-axis direction and the like. The second movable member 80 is movable in such as the Y-axis direction and the like.

In the fourteenth embodiment, the drive system 77 includes a rotary drive device rotating the table 78, a first drive device moving the first movable member 79, and a second drive device moving the second movable member 79.

In the fourteenth embodiment, by moving the first and second movable members 79 and 80, the table 78 is movable in five directions, i.e. the X-axis, Y-axis, θX, θY and θZ directions. In the fourteenth embodiment, the table 78 almost does not move in the Z-axis direction. Further, the table 78 can also be movable in six directions, i.e. the X-axis, Y-axis, Z-axis, θX, θY and θZ directions.

In the fourteenth embodiment, the drive system 77 of the first stage device 74 has an actuator with a higher resolution than that or the actuator of the drive system of the second stage device 75. In the fourteenth embodiment, the drive system 77 includes the actuator operating on Lorentz force such as a linear motor, a planar motor, a voice coil motor, or the like.

Further, the drive system 77 of the first stage device 74 can alternatively have an actuator with the same resolution as that of the actuator of the drive system of the second stage device 75.

In the fourteenth embodiment, the detection apparatus 1 includes a measuring system 81 arranged in the first space SP1 to measure the position of the stage 76. In the fourteenth embodiment, the measuring system 81 includes an encoder system.

The measuring system 81 has a rotary encoder measuring the rotational amount of the table 78 (the position with respect to the θY direction), a linear encoder measuring the position of the first movable member 79, and a linear encoder measuring the position of the second movable member 14.

In the fourteenth embodiment, the measuring system 81 measuring the position of the stage 76 of the first stage device 74 has a higher resolution than that of the measuring system measuring the position of the stage of the second stage device 75. The resolution includes, for example, that of a scale member of the encoder system. The resolution of the scale member includes the scale resolution of the scale member. That is in the fourteenth embodiment, the scale resolution of the scale member of the measuring system 81 measuring the position of the stage 76 of the first stage device 74 is lower than that of the scale member of the measuring system measuring the position of the stage of the second stage device 75.

Further, the measuring system 81 measuring the position of the stage 76 of the first stage device 74 can alternatively have the same resolution as that of the measuring system measuring the position of the stage of the second stage device 75.

In the fourteenth embodiment, the temperature of at least part of the first stage device 74 arranged in the first space SP1 is controlled with the gas G supplied from the supply port 7 to the first space SP1.

Further, in the fourteenth embodiment, the temperature of at least part of the measuring system 81 arranged in the first space SP1 is controlled with the gas G supplied from the supply port 7 to the first space SP1.

Further, in addition, to the X-ray source 2, the first stage device 74, and the measuring system 81, the temperature of at least some of the other members arranged in the first space SP1 is also controlled with the gas G supplied from the supply port 7 to the first space SP1.

As explained above, in the fourteenth embodiment, it is also possible to restrain temperature change in the members including the X-ray source 2 contained in the internal space SP, and temperature change in the internal space SP per se.

Further, in the fourteenth embodiment, a discharge port can be provided to discharge the gas in the first space SP1.

Further, in the fourteenth embodiment, a supply port can be provided to supply the temperature-controlled gas to the second space SP2. Further, in the fourteenth embodiment, another discharge port can be provided to discharge the gas in the second space SP2.

Further, while the temperature-controlled gas is supplied to the X-ray source in the above first to fourteenth embodiments, it can alternatively be supplied to such as at least part of the stage device or at least part of the measuring system. For example, the temperature-controlled gas can be supplied to the scale member of the measuring system.

<Fifteenth Embodiment>

Next, a fifteenth embodiment will be explained. In the following explanations, the same reference numerals will be assigned to the constitutive parts or components which are the same as or equivalent to those of the embodiments described above, and the explanations of which will be simplified or omitted.

In the fifteenth embodiment, explanations will be made with respect to a structure manufacturing system provided with the detection apparatus 1 described above.

Figure 19:
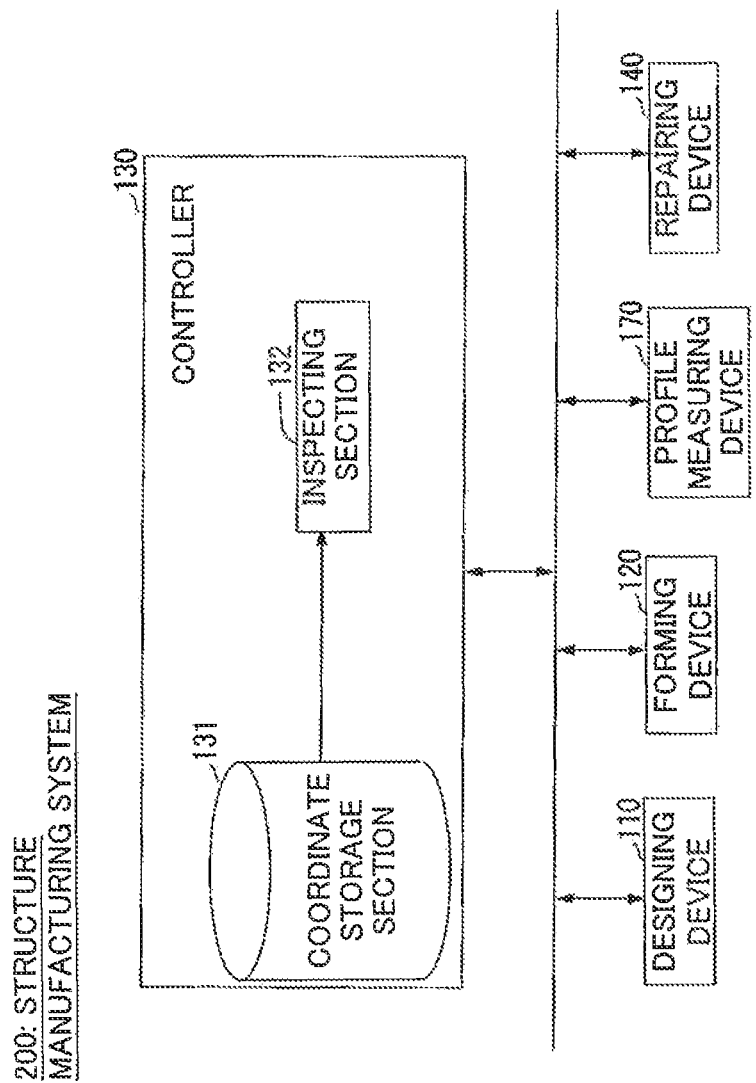
FIG. 19 is a view showing an example of a structural object manufacturing system provided with any of the above detection apparatuses.

FIG. 19 is a block diagram of a structure manufacturing system 200. The structure manufacturing system 200 includes the aforementioned detection apparatus 1, a forming device 120, a controller 130 an inspection device), and a repairing device 140. In the fifteenth embodiment, the structure manufacturing system 200 manufactures molded components such as automobile door parts, engine components, gear components, electronic components including circuit substrates, and the like.

A designing device 110 creates design information about the profile of a structure, and sends the created design information to the forming device 120. Further, the designing device 110 stores the created design information into an aftermentioned coordinate storage portion 131 of the controller 130. The design information mentioned here indicates the coordinates of each position of the structure. The forming device 120 fabricates the structure based on the design information inputted from the designing device 110. The formation process of the forming device 120 includes at least one of casting, forging, and cutting.

The detection apparatus 1 sends information indicating measured coordinates to the controller 130. The controller 130 includes the coordinate storage section 131 and an inspection section 132. The coordinate storage section 131 stores the design information from the designing device 110. The inspection section 132 reads out the design information from the coordinate storage section 131. The inspection section 132 creates information (profile information) signifying the fabricated structure from the information indicating the coordinates received from the detection apparatus 1. The inspection section 132 compares the information (the profile information) indicating the coordinates received from a profile measuring device 170 with the design information read out from the coordinate storage section 131. Based on the comparison result, the inspection section 132 determines whether or not the structure is formed in accordance with the design information. In other words, the inspection section 132 determines whether or not the fabricated structure nondefective. When the structure is not formed in accordance with the design information, then the inspection section 132 determines whether or not it is repairable. When it is repairable, then the inspection section 132 determines the defective portions and repairing amount based on the comparison result, and sends information to the repairing device 140 to indicate the defective portions and repairing amount.

Based on the information indicating the defective portions and repairing amount received from the controller 130, the repairing device 140 processes the defective portions of the structure.

FIG. 20 is a flowchart showing a processing flow in the structure manufacturing system 200. First, the design device 110 creates design information about the profile of a structure (step S101). Next, the forming device 120 fabricates the structure based on the designing information (step S102). Then, the detection apparatus 1 measures the coordinates with respect to the profile of the structure (step S103). Then, the inspection section 132 of the controller 130 inspects whether or not the structure is fabricated in accordance with the design information by comparing the created profile information of the structure from the detection apparatus 1 with the above design information (step S104).

Next, the inspection section 132 of the controller 130 determines whether or not the fabricated structure is nondefective (step S105). When the fabricated structure is nondefective (step S105: Yes), then the structure manufacturing system 200 ends the process. On the other hand, when the fabricated structure is defective (step S105; No), then the inspection section 132 of the controller 130 determines whether or not the fabricated structure is repairable (step S106).

When the fabricated structure is repairable (step S106; Yes), then the repairing device 140 reprocesses the structure (step S107) and then the process returns to step S103. On the other hand, when the fabricated structure is not repairable (step S106: No) then the structure manufacturing system 200 ends the process. With that, the process of the flowchart is ended.

In the above manner, because the detection apparatus 1 in the above embodiments can correctly measure the coordinates of the structure, the structure manufacturing system 200 is able to determine whether or not the fabricated structure is nondefective. Further, when the structure is defective, the structure manufacturing system 200 is able to reprocess the structure to repair the same.

Further. In each of the above embodiments, it is possible to provide a first supply supplying a temperature-controlled gas to the X-ray source, and a second supply to supplying the temperature-controlled gas to at least part of the stage device. Alternatively, in each of the above embodiments, it is possible to provide a first supply port supplying a temperature-controlled gas to the X-ray source, and a third supply port supplying the temperature-controlled gas to at least part of the measuring system.

Further, in each of the above embodiments, at least when the X-ray XL is emitted from the X-ray source, a temperature-controlled gas is supplied to the X-ray source. However, even when the X-ray XL is emitted from the X-ray source, the supply and supply-stop of the temperature-controlled gas can be carried out based on such as the position of the stage retaining the measuring object. For example, when the stage is situated close to the X-ray source (when the distance between the stage and the X-ray source is a first distance in the Z-axis direction), then the temperature-controlled as is supplied to the X-ray source. On the other hand, when the stage is situated far from the X-ray source (when the distance between the stage and the X-ray source is a second distance longer than the first distance in the Z-axis direction), then it is possible to stop supplying the gas to the X-ray source. Alternatively, when the distance between the stage and the X-ray source in the Z-axis direction is shorter than a threshold value, then the temperature-controlled as is supplied to the X-ray source; on the other hand, when the distance is longer than the threshold value, then it is possible to stop supplying the gas to the X-ray source. In other words, the temperature-controlled gas is supplied to the X-ray source when detecting (measuring) the measuring object S at a high resolution, while it is possible to stop supplying the gas to the X-ray source when detecting (measuring) the measuring object S at a low resolution.

In the above embodiments, the X-ray XL emitted from the x-ray source is X-ray, and the detection apparatus 1 is the X-ray CT detection apparatus. However, present teaching is not necessarily limited to such a configuration. For example, the electro-magnetic radiation emitted from the X-ray source can be electro-magnetic radiation of which wavelength is different from that of X-rays. It goes without saying that the electro-magnetic radiation emitted from the X-ray source can be X-rays in a broad sense, including the ultrasoft X-ray, the soft X-ray, the X-ray, and the hard X-ray. In addition, as long as the electro-magnetic radiation has a penetration power enough to penetrate the measuring object, the wavelength of the electro-magnetic radiation emitted from the X-ray source can be shorter than or longer than that of the X-rays in a broad sense. Each of the elements as described in the above embodiments is applicable to an apparatus for using the electro-magnetic radiation other than the X-ray in a broad sense, as long as the apparatus is capable of detecting the electro-magnetic radiation other than the X-ray in a broad sense.

Further, while the detection apparatus 1 has an X-ray source in each of the above embodiments, the X-ray source can be an external device to the detection apparatus 1. In other words, it is possible that the X-ray source does not constitute at least one part of the detection apparatus.

Further, in each of the above embodiments, the measuring object S is not limited to a component for industrial use, but can be such as a human body. Further, in each of the above embodiments, the detection apparatus 1 can also be used for medical purposes.

In each of the above embodiments, the X-ray source and the detection apparatus are fixed in predetermined positions, and en image of the measuring object S is acquired by rotating the stage. However, the scanning method is not limited to this. It is possible to fix one of the X-ray source and the detection apparatus in a predetermined position, and let the other be movable. Further, it is also possible for both the X-ray source and the detection apparatus to be movable.

Further, it is possible to appropriately combine the requirements of the respective embodiments described above. Further, there are cases in which some of the constitutive parts are not used.

What is claimed is:

1. A profile measuring apparatus configured to measure a profile of an object by irradiating the object with an X-ray and detecting a transmission X-ray transmitted through the object, comprising:
   a chamber member defining a first space, and configured to prevent the X-ray from leaking outside of the chamber;
   an X-ray source located in the first space and configured to irradiate the X-ray toward the object, including:
      a target configured to generate the X-ray by collision of electrons or transmission of electrons, an electron conduction member configured to conduct the electrons to the target, and a housing accommodating at least a part of the target and the electron conduction member;
   a stage located in the first space and configured to hold the object;
   a detector located in the first space and configured to detect at least a part of the transmission X-ray transmitted through the object; and
   a first supply port arranged in the first space at a position facing an outer surface of the housing or the target to supply a temperature-controlled gas to a part of the outer surface of the housing or the target.

2. The profile measuring apparatus according to claim 1, further comprising a first discharge port configured to discharge a part of a gas in the first space from the first space.

3. The profile measuring apparatus according to claim 1, further comprising a first control device configured to control a temperature of a gas, wherein the first supply port supplies the gas from the first control device.

4. The profile measuring apparatus according to claim 1, further comprising:
   a first control device configured to control a temperature of a gas; and
   a first discharge port configured to discharge, from the first space, a part of the gas in the first space,
   wherein the first control device controls the temperature of the gas discharged from the first discharge port, and the first supply port supplies the gas from the first control device.

5. The profile measuring apparatus according to claim 3, wherein the first control device is arranged in a second space different from the first space.

6. The profile measuring apparatus according to claim 4, wherein the first control device is arranged in a second space different from the first space.

7. The profile measuring apparatus according to claim 6, further comprising a temperature sensor configured to detect a temperature of one of the X-ray source and the first space,
   wherein the first control device controls the temperature of the gas supplied from the first control device based on a detection result of the temperature sensor.

8. A profile measuring apparatus configured to measure a profile of an object by irradiating the object with an X-ray and detecting a transmission X-ray transmitted through the object, comprising:
   a chamber member defining a first space, and configured to prevent the X-ray from leaking outside of the chamber;
   an X-ray source located in the first space and configured to irradiate the X-ray toward the object, including:
      a target configured to generate the X-ray by collision of electrons or transmission of electrons, an electron conduction member configured to conduct the electrons to the target, and a housing accommodating at least a part of the target and the electron conduction member;
   a stage located in the first space and configured to hold the object;
   a detector located in the first space and configured to detect at least a part of the transmission X-ray transmitted through the object; and
   a temperature-controlled member which is arranged in the first space at a position facing an outer surface of the housing or the target, and of which temperature is controlled, wherein a gas of which temperature is controlled through contact with the temperature-controlled member is supplied to a part of the outer surface of the housing or the target.

9. The profile measuring apparatus according to claim 8, wherein the temperature-controlled member includes a Peltier element.

10. The profile measuring apparatus according to claim 8, further comprising a liquid supply device configured to supply a temperature-controlled liquid to the temperature-controlled member,
wherein the temperature of the temperature-controlled member is controlled by the temperature-controlled liquid.

11. The profile measuring apparatus according to claim 10, further comprising a temperature sensor configured to detect a temperature of one of the X-ray source and the first space,
wherein the liquid supply device controls the temperature of the temperature-controlled liquid based on a detection result of the temperature sensor.

12. The profile measuring apparatus according to claim 8, further comprising a second control device configured to control a temperature of a part of the chamber member.

13. The profile measuring apparatus according to claim 12, further comprising a member which is fitted to the chamber member and has a lower thermal conductivity than that of the chamber member.

14. The profile measuring apparatus according to claim 1, wherein the housing includes an inner-duct in the outer surface of the housing, and
the profile measuring apparatus further comprising a third control device configured to supply a temperature-controlled fluid to the inner-duct.

15. The profile measuring apparatus according to claim 8, wherein the housing includes an inner-duct in the outer surface of the housing, and
the profile measuring apparatus further comprising a third control device configured to supply a temperature-controlled fluid to the inner-duct.

16. The profile measuring apparatus according to claim 14, further comprising a temperature sensor configured to detect a temperature of one of the X-ray source and the first space, wherein the third control device controls the temperature of the fluid based on a detection result of the temperature sensor.

17. The profile measuring apparatus according to claim 15, further comprising a temperature sensor configured to detect a temperature of one of the X-ray source and the first space, wherein the third control device controls the temperature of the fluid based on a detection result of the temperature sensor.

18. A method for measuring a profile of an object comprising:
preparing a chamber defining a first space by surrounding the first space;
holding the object by a stage located in the first space;
irradiating the object with an X-ray from an X-ray source arranged in the first space, the X-ray source including a target configured to generate the X-ray by collision of electrons or transmission of electrons, an electron conduction member configured to conduct the electrons to the target, and a housing accommodating at least a part of the target and the electron conduction member, and the housing including an inner-duct in an outer surface of the housing in which a temperature-controlled fluid is supplied;
detecting a transmission X-ray transmitted through the object by a detector located in the first space; and supplying a temperature-controlled gas to at least part of the X-ray source from a first supply port arranged in the first space at a position facing the outer surface of the housing or the target.

19. A structure manufacturing method comprising:
creating design information with respect to a profile of a structure;
forming the structure based on the design information;
measuring the profile of the formed structure by using the method according to claim 18; and
comparing the profile information obtained in the measuring with the design information.

20. The structure manufacturing method according to claim 19 further comprising repairing the structure, carried out based on a comparison result of the comparing.

21. The structure manufacturing method according to claim 20, wherein in the repairing, forming the structure is carried out over again.

22. The profile measuring apparatus according to claim 1, wherein the first supply port is configured to supply the temperature-controlled gas to a portion of the outer surface of the housing covering the electron conduction member.

23. The profile measuring apparatus according to claim 1, wherein the first supply port is configured to supply the temperature-controlled gas to a portion of the outer surface of the housing covering the target.

24. The profile measuring apparatus according to claim 1, wherein the first supply port is configured to supply the temperature-controlled gas to a portion of the outer surface of the housing near the target.

25. The profile measuring apparatus according to claim 1, wherein the first supply port is configured to supply the temperature-controlled gas to a portion of the target not being covered by the outer surface of the housing.

26. The profile measuring apparatus according to claim 1, wherein the electron conduction member includes an electron lens or a polariscope.

27. The profile measuring apparatus according to claim 1, wherein the X-ray generated by the X-ray source is irradiated toward the object in a plurality of irradiation directions to generate a plurality of transmission X-rays, and
the detector detects the plurality of transmission X-rays to measure the profile of the object.

28. The profile measuring apparatus according to claim 27, wherein the X-ray source and the detector are fixed,
the object held by the stage is rotated by rotating the stage, and
the irradiation directions of the X-ray with respect to the object is rotated by the rotation of the stage.

29. The profile measuring apparatus according to claim 1, wherein the X-ray source is fixed.

30. A method for measuring a profile of an object comprising:
preparing a chamber defining a first space by surrounding the first space;
holding the object by a stage located in the first space;
irradiating the object with an X-ray from an X-ray source arranged in the first space, the X-ray source including a target configured to generate the X-ray by collision of electrons or transmission of electrons, an electron conduction member configured to conduct the electrons to the target, and a housing accommodating at least a part of the target and the electron conduction member, and the housing including an inner-duct in an outer surface of the housing in which a temperature-controlled fluid is supplied;

detecting a transmission X-ray transmitted through the object by a detector located in the first space;
controlling a temperature of a temperature-controlled member which is arranged in the first space at a position facing an outer surface of the housing or the target; and
supplying a gas of which temperature is controlled through contact with the temperature-controlled member is supplied to a part of the outer surface of the housing or the target.

* * * * *